United States Patent
Cahill et al.

(10) Patent No.: US 11,458,203 B2
(45) Date of Patent: Oct. 4, 2022

(54) PHARMACEUTICAL COMPOSITIONS COMPRISING CAFFEIC ACID CHELATES

(71) Applicant: Arizona Board of Regents, on behald of Arizona State University, Scottsdale, AZ (US)

(72) Inventors: Thomas Cahill, Glendale, AZ (US); Jeffrey Langland, Chandler, AZ (US); Bertram Jacobs, Tempe, AZ (US); Carl Wagner, Glendale, AZ (US); Guillermo Ruiz, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/612,222

(22) PCT Filed: May 8, 2018

(86) PCT No.: PCT/US2018/031538
§ 371 (c)(1),
(2) Date: Nov. 8, 2019

(87) PCT Pub. No.: WO2018/208739
PCT Pub. Date: Nov. 15, 2018

(65) Prior Publication Data
US 2020/0171331 A1    Jun. 4, 2020

Related U.S. Application Data

(60) Provisional application No. 62/503,276, filed on May 8, 2017.

(51) Int. Cl.
*A61K 31/192* (2006.01)
*A61K 31/216* (2006.01)
(Continued)

(52) U.S. Cl.
CPC .......... *A61K 47/547* (2017.08); *A61K 31/192* (2013.01); *A61K 31/216* (2013.01); *A61P 31/20* (2018.01); *A61P 31/22* (2018.01)

(58) Field of Classification Search
CPC ...... A61K 31/216; A61K 31/192; A61P 31/22
(Continued)

(56) References Cited

U.S. PATENT DOCUMENTS 6,372,455 B1   4/2002   Jacobs et al.
6,750,043 B2   6/2004   Jacobs et al.
(Continued)

FOREIGN PATENT DOCUMENTS

CN    101085129 A  *  12/2007
EP    2135512 A1  *  12/2009  ............... A23L 1/30
(Continued)

OTHER PUBLICATIONS

Peterhans "Oxidant and antioxidant in viral disease: Disease Mechanism and Metabolism regulation,"American Soc. Nutritional Science, 1997, Supplement, pp. 962S-965S (Year: 1997).*
(Continued)

*Primary Examiner* — Shengjun Wang
(74) *Attorney, Agent, or Firm* — Riverside Law, LLP

(57) ABSTRACT

The present disclosure relates to pharmaceutical compositions comprising caffeic acid chelates, kits, and methods for using such compounds and pharmaceutical compositions.

2 Claims, 10 Drawing Sheets

(51) Int. Cl.
*A61K 47/54* (2017.01)
*A61P 31/22* (2006.01)
*A61P 31/20* (2006.01)

(58) Field of Classification Search
USPC .................................... 514/532, 533, 570
See application file for complete search history.

(56) References Cited

U.S. PATENT DOCUMENTS

| | | | |
|---|---|---|---|
| 6,942,855 | B2 | 9/2005 | Jacobs et al. |
| 10,293,012 | B2 | 5/2019 | Langland et al. |
| 2006/0099181 | A1 | 5/2006 | Jacobs et al. |
| 2007/0036758 | A1 | 2/2007 | Jacobs et al. |
| 2013/0295675 | A1 | 11/2013 | Jacobs et al. |
| 2014/0179747 | A1* | 6/2014 | Lewis, II ............ A61K 8/4926 514/356 |
| 2014/0377870 | A1 | 12/2014 | Jacobs et al. |
| 2019/0183947 | A1 | 6/2019 | Jacobs et al. |

FOREIGN PATENT DOCUMENTS

| | | |
|---|---|---|
| WO | WO 2002/085416 | 10/2002 |
| WO | WO 2002/086059 | 10/2002 |
| WO | WO 2005/007824 | 1/2005 |
| WO | WO 2005/074947 | 8/2005 |
| WO | WO 2011/156470 | 12/2011 |
| WO | WO 2016/012913 | 1/2016 |
| WO | WO 2016/123223 | 8/2016 |
| WO | WO 2017/205674 | 11/2017 |

OTHER PUBLICATIONS

Oniga et al. Evaluation onf phenolic acid derivatives and essential oil content in some *Melissa officinalis* L. varieties, Farmacia, 2010, vol. 58, No. 6, pp. 764-769. (Year: 2010).*

Tan et al. "Ebola virus disease: potential use of melatonin as treatment," J. Pineal Res. , 2014, vol. 57, pp. 381-384, (Year: 2014).*

CN 101085129A Abstract, Derwent-ACC-No. 2008-K47156 (Year: 2007).*

EP2135512A1 Abstract. Derwent-ACC-No. 2009-557886 (Year: 2009).*

Andjelkovic, M. et al. "Iron-Chelation Properties of Phenolic Acids bearing Catechol and Galloyl Groups", In Food Chemistry, vo. 98, No. 1, Mar. 2005, pp. 23-31.

Astani, A. et al., "Attachment and Penetration of Acyclovir-Resistant Herpes Simplex Virus are Inhibited by Melissa Officinalis Extract", In Phytotherapy Research, vol. 28, No. 10, May 2014, pp. 1547-1552.

Astani, A. et al., "Melissa Officinalis Extract Inhibits Attachment of Herpes Simplex Virus in Vitro", In Chemotherapy, vol. 58, No. 1, Feb. 2012, pp. 70-77.

Bailly, F. et al., "Anti-HIV Activities of Natural Antioxidant Caffeic Acid Derivatives: Toward an Antiviral Supplementation Diet", In Current Medicinal Chemistry, vol. 12, No. 15, Jul. 2005, pp. 1811-1818.

Bengali, Z. et al., "Vaccinia Virus Strain Differences in Cell Attachment and Entry", In Virology, vol. 389, Nos. 1-2, May 2009, pp. 132-140.

Charvat, T.T. et al., "Design, Synthesis, and Biological Evaluation of Chicoric Acid Analogs as Inhibitors of HIV-1 Integrase", In Bioorganic & Medicinal Chemistry, vol. 13, No. 14, Mar. 2006, pp. 4552-4567.

Denzler, K. et al., "Melissa Officinalis Extract Inhibits Herpes Simplex Virus-1 Glycoprotein B Interaction with Heparin Sulfate", In Herbal Medicine: Open Access, Apr. 2016, vol. 2, No. 2, pp. 1-13.

Dubois, M. et al., "Reaction of Rosmarinic Acid with Nitrite Ions in Acidic Conditions: Discovery of Nitro- and Dinitrorosmarinic Acids as New Anti-HIV-1 Agents", In Journal of Medicinal Chemistry, vol. 51, No. 8, Apr. 2008, pp. 2575-2579.

Genaro-Mattos, T.C. et al., "Antioxidant Activity of Caffeic Acid against Iron-Induced Free Radical Generation—A Chemical Approach", In Plos One, vol. 10, No. 6, Jun. 2015, pp. 1-12.

Hider, R.C. et al., "Metal Chelation of Polyphenols", In Flavonoids and Other Polyphenols, vol. 335, 2001, pp. 190-203.

Hirai, T. et al., "Effects of Some Naturally Occurring Iron Ion Chelators on In Vitro Superoxide Radical Formation", In Biological Trace Element Research, vol. 108, Dec. 2005, pp. 77-85.

International Premliminary Report on Patentabiliy dated Nov. 21, 2019 in International Patent Application No. PCT/US2018/031538, pp. 1-9.

International Search Report and Written Opinion dated Sep. 17, 2018 in International Patent Application No. PCT/US2018/031538, pp. 1-12.

Karaliota, A. et al., "Molybdenum Catecholates as Models for Mo in Biological Systems. 1. Synthesis and Spectroscopic Study on Mo Complexes with 3,4-dihydroxybenzoic and 3.4-dihydroxyphenylacetic Acid", In Journal of Inorganic Biochemistry, vol. 69, Nos. 1-2, Feb. 1998, pp. 79-90.

Khokhar, S. et al., "Iron Binding Characteristics of Phenolic Compounds: Some Tentative Structure-Activity Relations", In Food Chemistry, vol. 81, No. 1, May 2003, pp. 133-140.

King, P.J. et al., "Structure-Activity Relationships: Analogues of the Dicaffeoylquinic and Dicaffeoyltartaric Acids as Potent Inhibitors of Human Immunodeficiency Virus Type 1 Integrase and Replication", In Journal of Medicinal Chemistry, vol. 42, No. 3, Jan. 1999, pp. 497-509.

Kontoghiorghe, C.N. et al., "Phytochelators Intended for Clinical Use in Iron Overload, Other Diseases of Iron Imbalance and Free Radical Pathology", In Molecules, vol. 20, No. 11, Sep. 2015, pp. 20841-20872.

Lin Z.W. et al., "Chicoric Acid Analogues as HIV-1 Integrase Inhibitors", In Journal of Medicinal Chemistry, vol. 42, No. 8, Apr. 1999, pp. 1401-1414.

Louvel, S. et al., "Identification of Compounds from the Plant Species *Alepidea amatymbica* Active Against HIV", In South African Journal of Botany, vol. 86, May 2013, pp. 9-14.

Mahmood, N. et al., "Inhibition of HIV-Infection by Caffeoylquinic Acid-Derivatives", In Antiviral Chemistry & Chemotherapy, vol. 4, No. 4, Aug. 1993, pp. 235-240.

Mazzanti, G. et al., "Inhibitory Activity of *Melissa officinalis* L. Extract on Herpes Simplex Virus Type 2 Replication", In Natural Product Research, vol. 22, No. 16, Feb. 2008, pp. 1433-1440.

Moran, J.F. et al., "Complexes of Iron with Phenolic Compounds from Soybean Nodules and Other Legume Tissues: Prooxidant and Antioxidant Properties", In Free Radical Biology and Medicine, vol. 22, No. 5, Aug. 1997, pp. 861-870.

Mukherjee, H. et al., "Anti-Herpes Virus Activities of *Achyranthes aspera*: An Indian Ethnomedicine, and its Triterpene Acid", In Microbiological Research, May 2013, pp. 1-7.

O'Hearn, A. et al., "Role of EXT1 and Glycosaminoglycans in the Early Stage of Filovirus Entry", In Journal of Virology, vol. 89, No. 10, Mar. 2015, pp. 5441-5449.

Petersen, M. et al., "Molecules of Interest—Rosmarinic Acid", In Phytochemistry, vol. 62, No. 2, Sep. 2003, pp. 121-125.

Petrou, A.L. et al., "Coordination-Complexes of 3,4-dihydroxyphenylpropionic Acid (dihydrocaffeic acid) with Copper(II), Nickel(II), Cobalt(II) and Iron(III)", In Transition Metal Chemistry, vol. 16, No. 1, Feb. 1991, pp. 48-52.

Rice-Evans, C.A. et al., "Structure-Antioxidant Activity Relationships of Flavonoids and Phenolic Acids", In Free Radical Biology and Medicine, vol. 20, No. 7, Dec. 1995, pp. 933-956.

Shakeri, A. et al., "*Melissa officinalis* L.—A Review of its Traditional Uses, Phytochemistry and Pharmacology", In Journal of Ethnopharmacology, vol. 188, Jul. 2016, pp. 204-228.

Swarup, V. et al., "Antiviral and Anti-Inflammatory Effects of Rosmarinic Acid in an Experimental Murine Model of Japanese Encephalitis", In Antimicrobial Agents and Chemotherapy, vol. 51, No. 7, Sep. 2007, pp. 3367-3370.

(56) References Cited

OTHER PUBLICATIONS

Tewtrakul, S. et al., "HIV-1 Integrase Inhibitory Substances from Coleus Parvifolius", In Phytotherapy Research, vol. 17, No. 3, Mar. 2003, pp. 232-239.

* cited by examiner

PHARMACEUTICAL COMPOSITIONS COMPRISING CAFFEIC ACID CHELATES

BACKGROUND

Caffeic acid and related compounds with the caffeoyl moiety (e.g. rosmarinic acid, chicoric acid, etc.) have been shown to have antiviral activity [1-3]. These compounds are effective against herpes simplex viruses (HSV)[4] and human immunodeficiency virus (HIV)[5-9]. The presumptive mechanism of action for HSV is thought to act by inhibiting viral-host cell interaction[1, 4, 10]. Many of these compounds have been isolated from natural sources, but synthetic analogs have also been created and evaluated for antiviral properties [5, 11-13].

Previous work using extracts from the botanical *Melissa officinalis* (common name: lemon balm) have reported antiviral properties [4, 10, 14] and have shown the presence of multiple organic acids with the caffeoyl moiety. These caffeoyl moiety containing organic acids are presumed to be the active antiviral constituent(s) present in *M. officinalis* extracts. These extracts have been shown to directly inhibit HSV1 virions by binding to glycoprotein B (gB) within the virion structure and inhibiting attachment to heparin sulfate proteoglycans on the cell surface [10].

Caffeic acid and related compounds contain a catechol functional group, which is a well-known metal chelation functional group [15-19]. It is hypothesized that the chelation of a metal enhances, or is essential, to the activity of the caffeic acid compounds, however the role of metal chelation has never been assessed in regard to the antiviral properties of these compounds.

SUMMARY

The present disclosure relates to pharmaceutical compositions comprising caffeic acid chelates, kits, and methods for using such compounds and pharmaceutical compositions.

DETAILED DESCRIPTION

Figure 1:
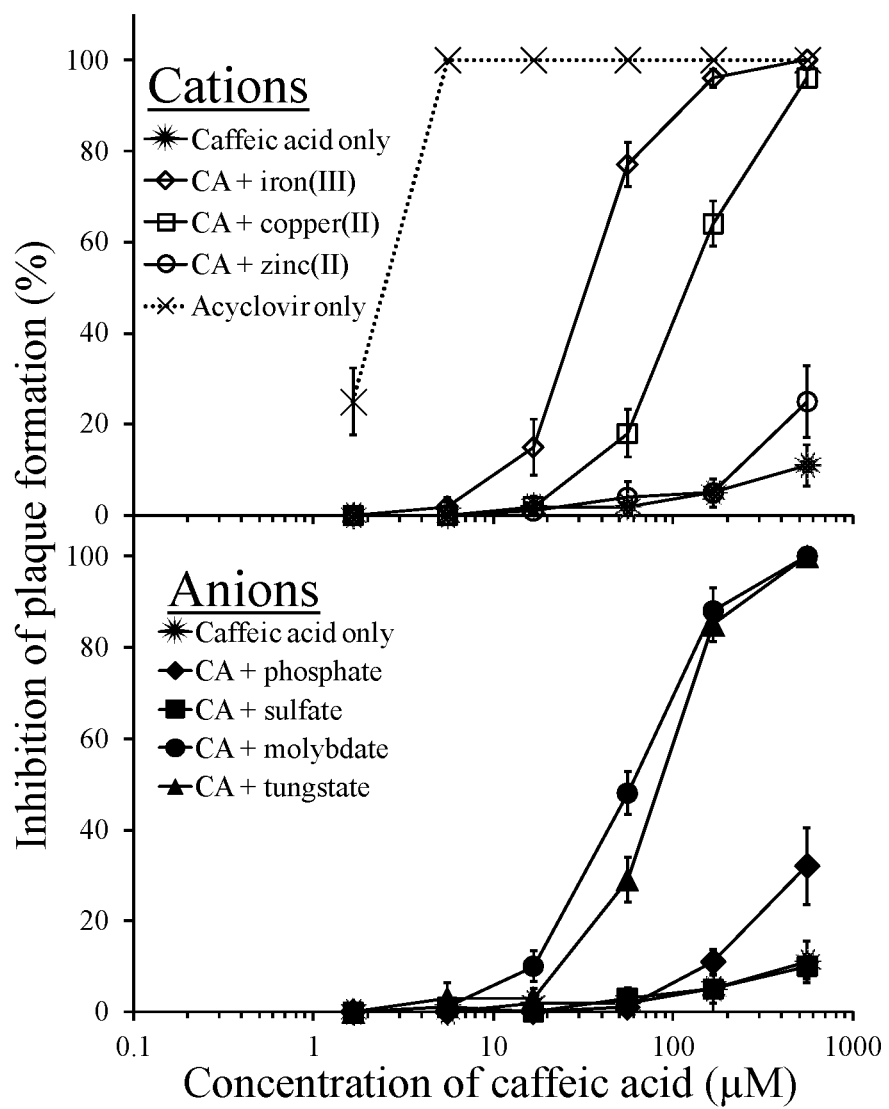
FIG. 1 shows the HSV1 antiviral activity expressed as the inhibition of plaque formation (mean % relative to controls±standard error, n=3 per point) of caffeic acid (CA) paired with different inorganic cationic and anionic ions that may form complexes with caffeic acid. All the inorganic ions were added at a half molar ratio to caffeic acid. The "acyclovir only" treatment was a positive control as well as benchmark standard.

The disclosure includes the following:

1. A pharmaceutical composition comprising
   (a) an effective amount of a chelate of a compound of formula (I); and
   (b) a pharmaceutically acceptable carrier;
   wherein the compound of formula (I) is

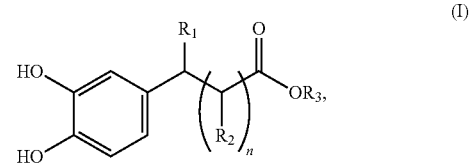

wherein $R_1$ and $R_2$ are independently H or OH, or $R_1$ and $R_2$ are taken together to form a double bond;

$R_3$ is H or a conjugate with an acid selected from the group consisting of 2-(3,4-dihydroxyphenyl)-2-hydroxyacetic acid, danshensu acid, a sugar acid, tartaric acid, citric acid or caftaric acid;

n is 0 or 1; and wherein the chelate comprises an ion selected from the group consisting of is an $Fe^{+3}$, $Ni^{+2}$, $Zn^{+2}$, $Mn^{+2}$, $Al^{+3}$, $Cu^{+2}$, $(PO_4)^{-3}$, $(SO_4)^{-2}$, $(MoO_4)^{-2}$, $(WO_4)^{-2}$, $(BiO_3)^-$ and combinations thereof.

2. A pharmaceutical composition comprising
(a) an effective amount of a chelate of a compound of formula (I); and
(b) a pharmaceutically acceptable carrier;
wherein the compound of formula (I) is

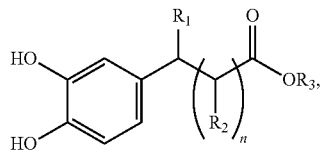

wherein $R_1$ and $R_2$ are independently H or OH, or $R_1$ and $R_2$ are taken together to form a double bond;
$R_3$ is H or a conjugate with an acid selected from the group consisting of 2-(3,4-dihydroxyphenyl)-2-hydroxyacetic acid, danshensu acid, a sugar acid, tartaric acid, citric acid or caftaric acid;
n is 0 or 1; and
wherein the chelate comprises an ion selected from the group consisting of is an $Fe^{+3}$, $Ni^{+2}$, $Zn^{+2}$, $Mn^{+2}$, $Al^{+3}$, $Cu^{+2}$, $(PO_4)^{-3}$, $(SO_4)^{-2}$, $(MoO_4)^{-2}$, $(WO_4)^{-2}$, $(BiO_3)^{-}$ and combinations thereof,
provided that, when n is 1, $R_1$ and $R_2$ are taken together to form a double bond and $R_3$ is H, the ion is not $Fe^{+3}$.

3. A pharmaceutical composition comprising
(a) an effective amount of a chelate of a compound of formula (I); and
(b) a pharmaceutically acceptable carrier;
wherein the compound of formula (I) is

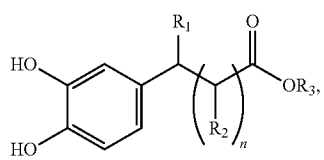

wherein $R_1$ and $R_2$ are H or are taken together to form a double bond;
$R_3$ is H or a conjugate with an acid selected from the group consisting of danshensu acid, a sugar acid, tartaric acid, citric acid or caftaric acid;
n is 0 or 1; and
wherein the chelate comprises an ion selected from the group consisting of is an $Fe^{+3}$, $Ni^{+2}$, $Zn^{+2}$, $Mn^{+2}$, $Al^{+3}$, $Cu^{+2}$, $(PO_4)^{-3}$, $(SO_4)^{-2}$, $(MoO_4)^{-2}$, $(WO_4)^{-2}$, $(BiO_3)^{-}$ and combinations thereof.

4. A pharmaceutical composition comprising
(a) an effective amount of a chelate of a compound of formula (I); and
(b) a pharmaceutically acceptable carrier;
wherein the compound of formula (I) is

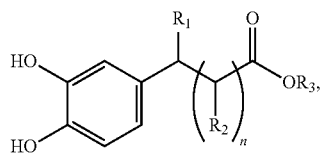

wherein $R_1$ and $R_2$ are H or are taken together to form a double bond;
$R_3$ is H, danshensu acid, a sugar acid, tartaric acid, citric acid or caftaric acid;
n is 0 or 1; and
wherein the chelate comprises an ion selected from the group consisting of is an $Fe^{+3}$, $Ni^{+2}$, $Zn^{+2}$, $Mn^{+2}$, $Al^{+3}$, $Cu^{+2}$, $(PO_4)^{-3}$, $(SO_4)^{-2}$, $(MoO_4)^{-2}$, $(WO_4)^{-2}$, $(BiO_3)^{-}$ and combinations thereof,
provided that, when n is 1, $R_1$ and $R_2$ are taken together to form a double bond and $R_3$ is H, the ion is not $Fe^{+3}$ 5. The pharmaceutical composition of any of the above 1. to 4., wherein, in the compound of formula (I), $R_1$ and $R_2$ are taken together to form a double bond.

6. The pharmaceutical composition of any of the above 1. to 4., wherein, in the compound of formula (I), $R_1$ and $R_2$ are H.

7. The pharmaceutical composition of any of the above 1. to 4., wherein, in the compound of formula (I), $R_1$ is H and $R_2$ is H.

8. The pharmaceutical composition of any one of the above 1. to 4., wherein, in the compound of formula (I), n is 0.

9. The pharmaceutical composition of any one of the above 1. to 4., wherein, in the compound of formula (I), n is 1.

10. The pharmaceutical composition of any one of the above 1. to 9., wherein $R_3$ is H.

11. The pharmaceutical composition of any one of the above 1. to 9., wherein $R_3$ is a conjugate with tartaric acid.

12. The pharmaceutical composition of any one of the above 1. to 9., wherein $R_3$ is a conjugate with caftaric acid.

13. The pharmaceutical composition of any one of the above 1. to 9., wherein $R_3$ is a conjugate with danshensu acid.

14. The pharmaceutical composition of any one of the above 1. to 9., wherein $R_3$ is a conjugate with a sugar acid.

15. The pharmaceutical composition of any one of the above 1. to 14., wherein the compound is selected from the group consisting of:

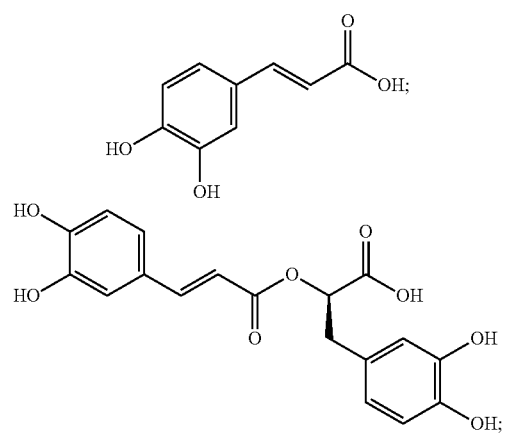

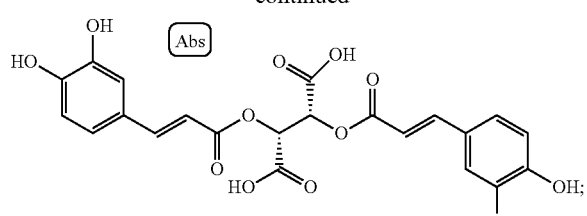

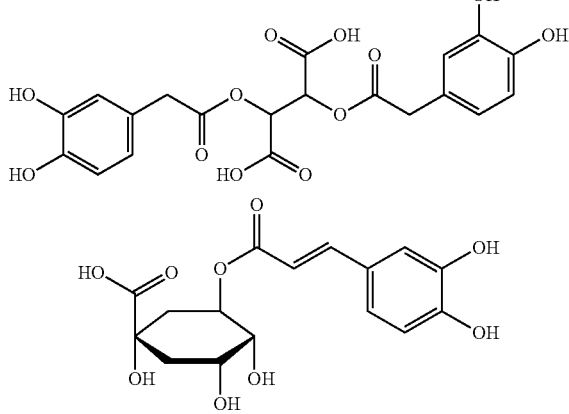

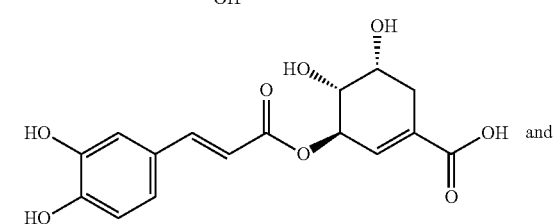

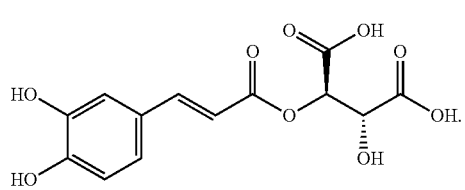

16. The pharmaceutical composition of any one of the above 1. to 14., wherein the compound is selected from the group consisting of:

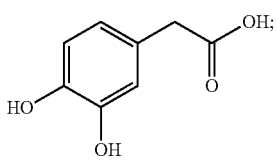

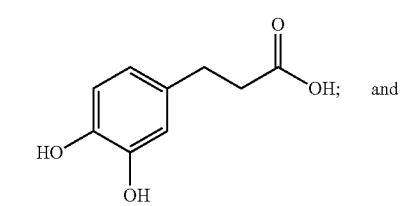

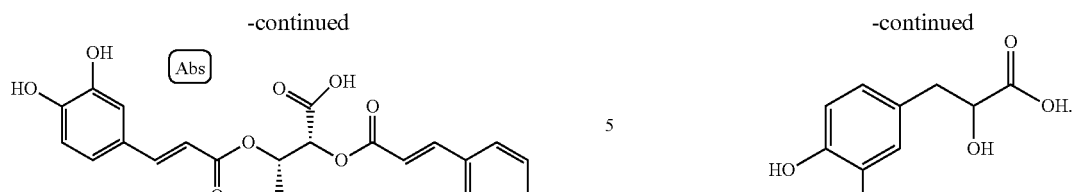

17. The pharmaceutical composition of any one of the above 1. to 14., wherein the compound is selected from the group consisting of:

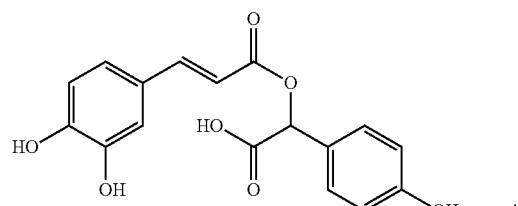

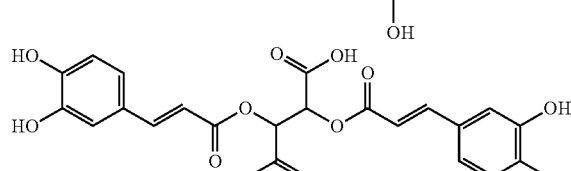

18. The pharmaceutical composition of any one of the above 1. to 17., wherein the chelate comprises an ion selected from the group consisting of is an $Fe^{+3}$, $Mn^{+2}$, $Al^{+3}$, $Cu^{+2}$, $(PO_4)^{-3}$, $(MoO_4)^{-2}$, $(WO_4)^{-2}$, $(BiO_3)^{-}$ and combinations thereof.

19. The pharmaceutical composition of any one of the above 1. to 17., wherein the chelate comprises an ion selected from the group consisting of an $Fe^{+3}$, $Mn^{+2}$, and $Al^{+3}$.

20. The pharmaceutical composition of any one of the above 1. to 17., wherein the chelate comprises an ion selected from the group consisting of $(PO_4)^{-3}$, $(MoO_4)^{-2}$ and $(WO_4)^{-2}$.

21. The pharmaceutical composition of the above 1. or 2., wherein the compound is

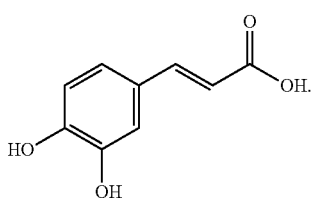 [SMILES: O=C(O)/C=C/c1ccc(O)c(O)c1]

22. The pharmaceutical composition of the above 21., wherein the ion is $Fe^{+3}$.

23. The pharmaceutical composition of any one of the above 1. to 22., further comprising a second therapeutic agent.

24. A method of treating a subject infected with herpes simplex virus, the method comprising administering to the subject a compound of formula (I) as defined in any one of the above 1. to 22., or a pharmaceutical composition of any one of the above 1. to 23. in an amount to treat infection by the herpes simplex virus in the subject.

25. A method of preventing infection of a subject with herpes simplex virus, the method comprising administering to the subject an effective amount of a compound of formula (I) as defined in any one of the above 1. to 22., or a pharmaceutical composition of any one of the above 1. to 23. prior to exposure of the subject to herpes simplex virus, thereby preventing infection with the herpes simplex virus.

26. A method of treating a subject infected with Ebola virus, the method comprising administering to the subject a compound of formula (I) as defined in any one of the above 1. to 22., or a pharmaceutical composition of any one of the above 1. to 23. in an amount to treat infection by the Ebola simplex virus in the subject.

27. A method of preventing infection of a subject with Ebola virus, the method comprising administering to the subject an effective amount of a compound of formula (I) as defined in any one of the above 1. to 22., or a pharmaceutical composition of any one of the above 1. to 23. prior to exposure of the subject to Ebola virus, thereby preventing infection with the Ebola virus.

28. A method of treating a subject infected with vaccinia virus, the method comprising administering to the subject a compound of formula (I) as defined in any one of the above 1. to 22., or a pharmaceutical composition of any one of the above 1. to 23. in an amount to treat infection by the vaccinia virus in the subject.

29. A method of preventing infection of a subject with vaccinia virus, the method comprising administering to the subject an effective amount of a compound of formula (I) as defined in any one of the above 1. to 22., or a pharmaceutical composition of any one of the above 1. to 23. prior to exposure of the subject to vaccinia virus, thereby preventing infection with the vaccinia.

30. A method of treating or preventing herpes simplex virus infection of a cell, the method comprising exposing herpes simplex virus or a herpes simplex virus-infected cell to an effective amount of a compound of formula (I) as defined in any one of the above 1. to 22., or a pharmaceutical composition of any one of the above 1. to 23., wherein the exposing inhibits entry of the herpes simplex virus into the cell.

31. A method of treating or preventing Ebola virus infection of a cell, the method comprising exposing Ebola virus or an Ebola virus-infected cell to an effective amount of a compound of formula (I) as defined in any one of the above 1. to 22., or a pharmaceutical composition of any one of the above 1. to 23., wherein the exposing inhibits entry of the Ebola virus into the cell.

32. A method of treating or preventing vaccinia infection of a cell, the method comprising exposing vaccinia virus or a vaccinia virus-infected cell to an effective amount of a compound of formula (I) as defined in any one of the above 1. to 22., or a pharmaceutical composition of any one of the above 1. to 23., wherein the exposing inhibits entry of the vaccinia virus into the cell.

33. The method of any of the above 30. to 32., wherein the cell is a human cell.

34. A use of the compound as defined in any one of the above 1. to 22. or use of the pharmaceutical composition of any one of the above 1. to 23. in the manufacture of a medicament for treating an HSV or Ebola viral infection.

35. The compound as defined in any one of the above 1. to 22. or the pharmaceutical composition of any one of the above 1. to 23. treating an HSV or Ebola viral infection.

36. A kit comprising the compound as defined in any one of the above 1. to 22., a container, and a package insert or label indicating that the compound can be used to treat an HSV, Ebola or vaccinia viral infection.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "caffeic acid" is also referred to as 3,4-dihydroxycinnamic acid.

The term "pharmaceutically acceptable carrier" refers to a diluent, adjuvant or excipient, with which a compound of the disclosure may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "effective amount" refers to an amount of a compound of the disclosure effective to treat a disease or disorder in a subject.

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state.

Those in need of treatment include those already having the condition or disorder as well as those prone to have the condition or disorder.

The term "subject" as used herein, includes, but is not limited to, a human, rat, mouse, guinea pig, monkey, pig, goat, cow, horse, dog, cat, bird and fowl. In some embodiments, the subject is a human.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

The caffeic acid chelates of the disclosure are non-naturally occurring (i.e., they are not found in nature).

The caffeic acid chelates are synthesized or man-made.

Caffeic Acid Chelates

Figure 3:
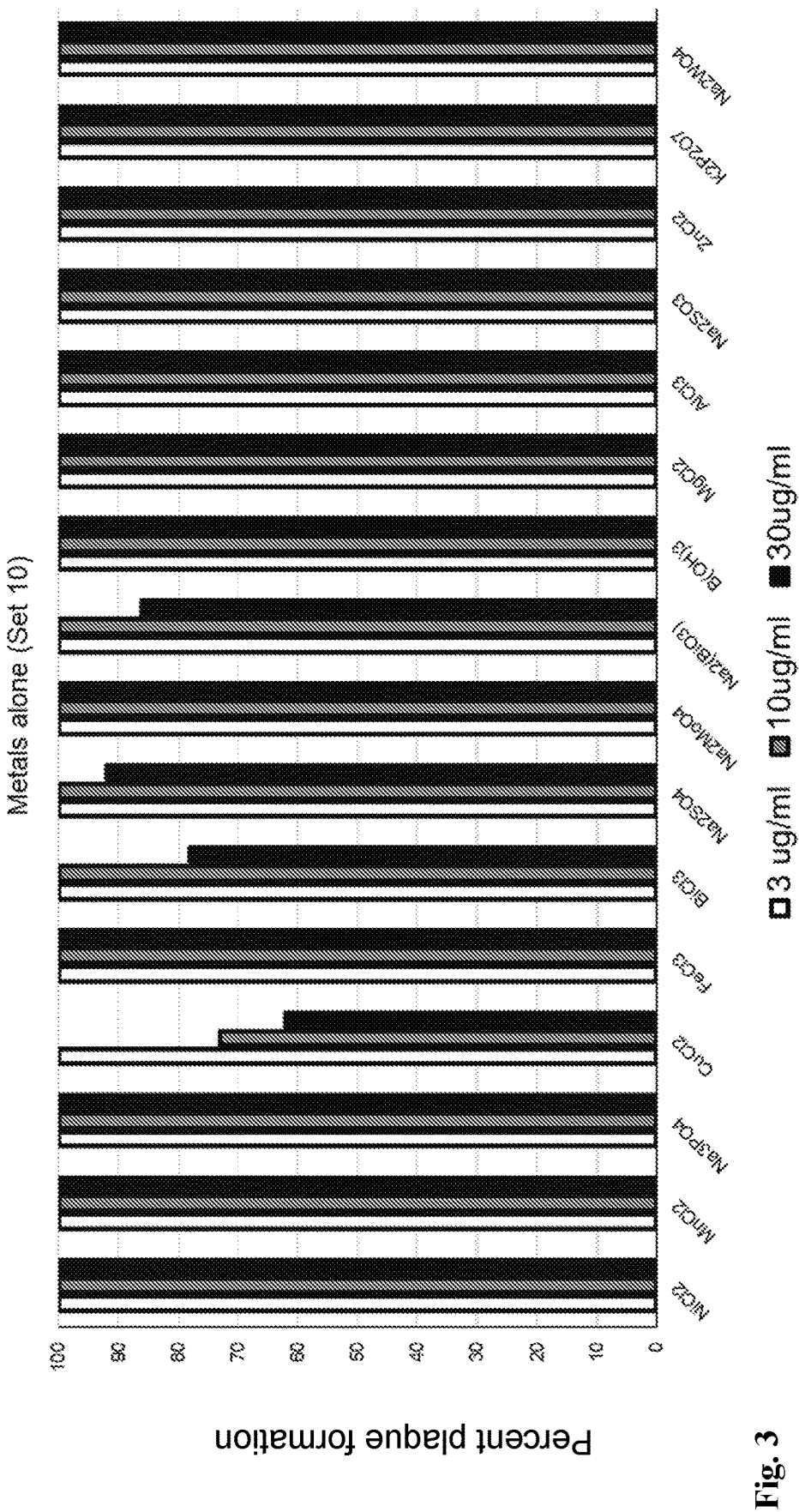

The present disclosure relates to caffeic acid chelates for use as an antiviral agent that is effective against Herpes Simplex Virus (HSV), Ebola Viruses and vaccinia. The caffeic acid chelates of the present disclosure are believed to inhibit the virus attachment to the cell and thus reduce viral infection of cells. These viruses bind cells via a heparin-sulfate proteoglycan receptor. This active constituent is believed to bind proteins on the surface of the virion thereby blocking interaction with the cellular receptor. This mechanism of action of the antiviral is different from current commonly used antiviral medications such as acyclovir. Given the common nature of both of the main components of the new antiviral agent, the compound is expected to have low cellular toxicity. Results from early studies have shown it to have an $IC_{50}$ of 65 to 90 um with a selectivity index (SI) greater than 38 (FIG. 3).

The caffeic acid chelate of the disclosure is represented by formula (I):

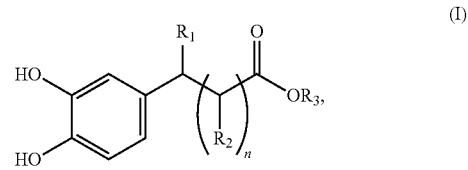

wherein $R_1$ and $R_2$ are independently H or OH, or $R_1$ and $R_2$ are taken together to form a double bond;

$R_3$ is H or a conjugate with an acid selected from the group consisting of 2-(3,4-dihydroxyphenyl)-2-hydroxyacetic acid, danshensu acid, a sugar acid, tartaric acid, citric acid or caftaric acid;

n is 0 or 1; and wherein the chelate comprises an ion selected from the group consisting of is an $Fe^{+3}$, $Ni^{+2}$, $Zn^{+2}$, $Mn^{+2}$, $Al^{+3}$, $Cu^{+2}$, $(PO_4)^{-3}$, $(SO_4)^{-2}$, $(MoO_4)^{-2}$, $(WO_4)^{-2}$, $(BiO_3)^-$ and combinations thereof.

In one embodiment, the caffeic acid chelate of the disclosure is represented by formula (I):

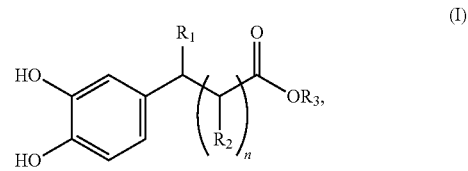

wherein $R_1$ and $R_2$ are independently H or OH, or $R_1$ and $R_2$ are taken together to form a double bond;

$R_3$ is H or a conjugate with an acid selected from the group consisting of 2-(3,4-dihydroxyphenyl)-2-hydroxyacetic acid, danshensu acid, a sugar acid, tartaric acid, citric acid or caftaric acid;

n is 0 or 1; and wherein the chelate comprises an ion selected from the group consisting of is an $Fe^{+3}$, $Ni^{+2}$, $Zn^{+2}$, $Mn^{+2}$, $Al^{+3}$, $Cu^{+2}$, $(PO_4)^{-3}$, $(SO_4)^{-2}$, $(MoO_4)^{-2}$, $(WO_4)^{-2}$, $(BiO_3)^-$ and combinations thereof, provided that, when n is 1, $R_1$ and $R_2$ are taken together to form a double bond and $R_3$ is H, the ion is not $Fe^{+3}$.

In one embodiment, $R_1$ and $R_2$ are taken together to form a double bond. In another embodiment, $R_1$ and $R_2$ are H. In another embodiment, $R_1$ is H and $R_2$ is OH.

In one embodiment, n is 0. In another embodiment, n is 1.

In one embodiment, $R_3$ is H. In another embodiment, $R_3$ is a conjugate with an acid selected from the group consisting of 2-(3,4-dihydroxyphenyl)-2-hydroxyacetic acid, tartaric acid, caftaric acid, danshensu acid, or a sugar acid. In another embodiment, $R_3$ is a conjugate with tartaric acid. In another embodiment, $R_3$ is a conjugate with caftaric acid. In another embodiment, $R_3$ is a conjugate with danshensu acid. In another embodiment, $R_3$ is a conjugate with a sugar acid. In another embodiment, $R_3$ is a conjugate with 2-(3,4-dihydroxyphenyl)-2-hydroxyacetic acid.

In one embodiment, $R_1$ is H and n is 0. In another embodiment, $R_1$ is H and n is 1.

In one embodiment, $R_1$ is H, n is 1 and $R_2$ is H. In another embodiment, $R_1$ is H, n is 1 and $R_2$ is OH. In another embodiment, $R_1$ and $R_2$ are taken together to form a double bond and n is 1.

In one embodiment, $R_1$ is H and $R_3$ is H. In another embodiment, $R_1$ is H and $R_3$ is a conjugate with an acid selected from the group consisting of 2-(3,4-dihydroxyphenyl)-2-hydroxyacetic acid, tartaric acid, caftaric acid, danshensu acid, or a sugar acid. In one aspect of this embodiment, $R_1$ is H and $R_3$ is a conjugate with 2-(3,4-dihydroxyphenyl)-2-hydroxyacetic acid. In another aspect of this embodiment, $R_1$ is H and $R_3$ is a conjugate with tartaric acid. In another aspect of this embodiment, $R_1$ is H and $R_3$ is a conjugate with caftaric acid. In another aspect of this embodiment, $R_1$ is H and $R_3$ is a conjugate with danshensu acid. In another aspect of this embodiment, $R_1$ is H and $R_3$ is a conjugate with a sugar acid.

In one embodiment, $R_2$ is H and $R_3$ is H. In another embodiment, $R_2$ is H and $R_3$ is a conjugate with an acid selected from the group consisting of 2-(3,4-dihydroxyphenyl)-2-hydroxyacetic acid, tartaric acid, caftaric acid, danshensu acid, or a sugar acid. In one aspect of this embodiment, $R_2$ is H and $R_3$ is a conjugate with 2-(3,4-dihydroxyphenyl)-2-hydroxyacetic acid. In another aspect of this embodiment, $R_2$ is H and $R_3$ is a conjugate with tartaric acid. In another aspect of this embodiment, $R_2$ is H and $R_3$ is a conjugate with caftaric acid. In another aspect of this embodiment, $R_2$ is H and $R_3$ is a conjugate with danshensu acid. In another aspect of this embodiment, $R_2$ is H and $R_3$ is a conjugate with a sugar acid.

In one embodiment, $R_1$ and $R_2$ are taken together to form a double bond and $R_3$ is H. In another embodiment, $R_1$ and $R_2$ are taken together to form a double bond and $R_3$ is a conjugate with an acid selected from the group consisting of 2-(3,4-dihydroxyphenyl)-2-hydroxyacetic acid, tartaric acid, caftaric acid, danshensu acid, or a sugar acid. In one aspect of this embodiment, $R_1$ and $R_2$ are taken together to form a double bond and $R_3$ is a conjugate with 2-(3,4-dihydroxyphenyl)-2-hydroxyacetic acid. In another aspect of this embodiment, $R_1$ and $R_2$ are taken together to form a double bond and $R_3$ is a conjugate with tartaric acid. In another aspect of this embodiment, $R_1$ and $R_2$ are taken together to form a double bond and $R_3$ is a conjugate with caftaric acid. In another aspect of this embodiment, $R_1$ and $R_2$ are taken together to form a double bond and $R_3$ is a conjugate with danshensu acid. In another aspect of this embodiment, $R_1$ and $R_2$ are taken together to form a double bond and $R_3$ is a conjugate with a sugar acid.

In one embodiment, the compound of formula (I) is selected from the group consisting of:

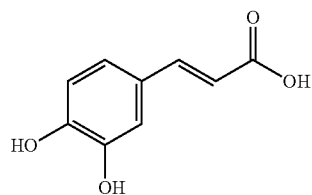

-continued

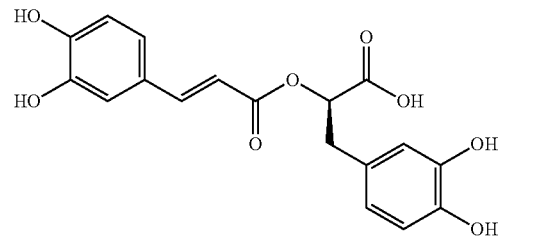

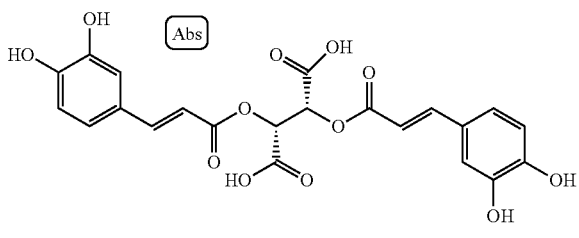

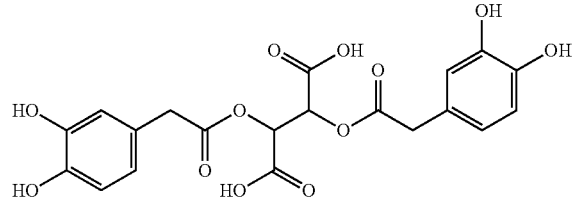

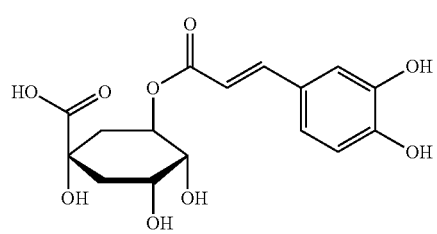

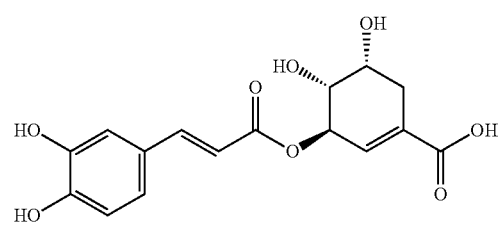

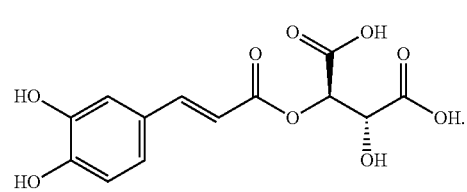

In one embodiment, the compound of formula (I) is selected from the group consisting of:

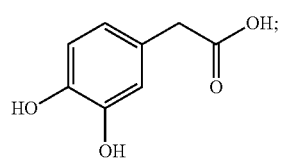

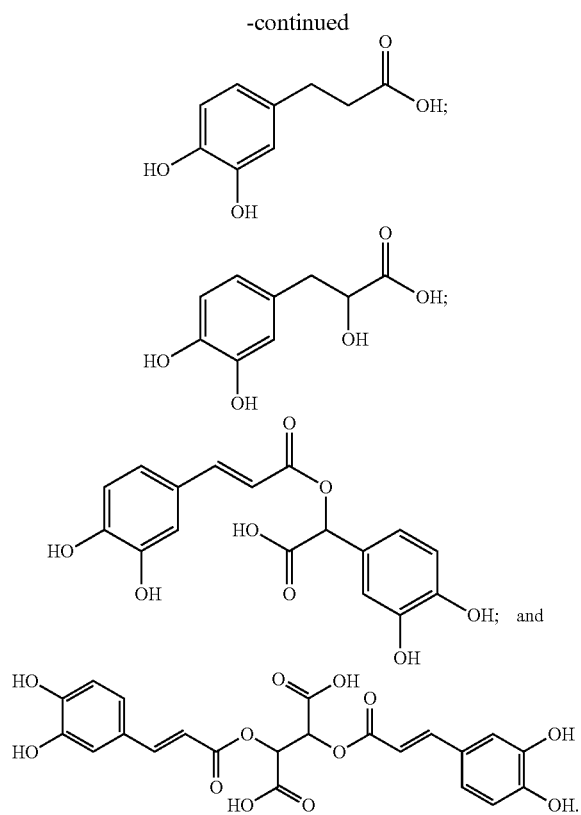

Pharmaceutical Compositions

According to one embodiment, the present disclosure provides a pharmaceutical composition comprising a caffeic acid chelate compound described herein and a pharmaceutically acceptable carrier.

The pharmaceutical composition of the disclosure may be formulated for administration in solid or liquid form, including those adapted for administration by oral, nasal, parenteral, rectal, topical, ocular, inhalation and intra-tumor administration. Parenteral administration includes subcutaneous injections, intravenous, intramuscular or intrasternal injection or infusion techniques. In one embodiment, the compositions are administered parenterally. In another embodiment, the compositions are administered intravenously. In another embodiment, the compositions are administered topically.

The pharmaceutical composition of the disclosure may be in the form of a liquid, e.g., a solution, emulsion or suspension, pellets, powders, sustained-release formulations, or any other form suitable for use. The pharmaceutical composition may comprise sterile diluents such as water, saline solution, preferably physiological saline, Ringer's solution, isotonic sodium chloride, fixed oils such as synthetic mono- or diglycerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids; agents for the adjustment of tonicity such as sodium chloride or dextrose; surfactants; preservatives; wetting agents; dispersing agents; suspending agents; stabilizers; solubilizing agents; local anesthetics, e.g., lignocaine; or isotonic agent.

It should be understood that a specific dosage and treatment regimen for any particular subject will depend upon a variety of factors, including the type of subject (e.g., human), the activity of the specific compound employed, the composition employed, the manner of administration, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

Preferably, the compositions are formulated so that a dosage of between about 0.01 to about 20 mg/kg body weight/day of the compound of formula (I) can be administered to a subject receiving the composition. In one embodiment, the dosage administered to the subject is between about 0.01 mg/kg and about 10 mg/kg of the subject's body weight. In another embodiment, the dosage administered to the subject is between about 0.1 mg/kg and about 10 mg/kg of the subject's body weight. In yet another embodiment, the dosage administered to the subject is between about 0.1 mg/kg and about 5 mg/kg of the subject's body weight. In yet another embodiment, the dosage administered is between about 0.1 mg/kg and about 3 mg/kg of the subject's body weight. In yet another embodiment, the dosage administered is between about 1 mg/kg and about 3 mg/kg of the subject's body weight.

The pharmaceutical compositions comprise an effective amount of a compound described herein such that a suitable dosage will be obtained. Typically, this amount is at least about 0.01% of a compound by weight of the composition. In a preferred embodiment, pharmaceutical compositions are prepared so that a parenteral dosage unit contains from about 0.01% to about 2% by weight of the compound of the disclosure.

For intravenous administration, the pharmaceutical composition may comprise from about 0.01 to about 100 mg of a compound described herein per kg of the subject's body weight. In one aspect, the composition may include from about 1 to about 100 mg of a compound described herein per kg of the subject's body weight. In another aspect, the amount administered will be in the range from about 0.1 to about 25 mg of a compound described herein per kg of body weight.

The pharmaceutical compositions of the present disclosure may optionally further comprise a second therapeutic agent in an effective amount. The second therapeutic agent includes those that are known and those discovered to be effective in the treatment of HSV or Ebola viral infections.

Methods of Use

The present disclosure also provides methods of using the compounds described herein or pharmaceutical compositions thereof. The compounds and compositions are useful for treating or preventing infections by herpesviridae, filoviridae or poxviridae. In one embodiment, the compounds and compositions are useful for treating or preventing infections by herpesviridae. In another embodiment, the compounds and compositions are useful for treating or preventing infections by HSV1, HSV2, Varicella Zoster virus, Epstein-Barr virus, or cytomegalovirus. In another embodiment, the compounds and compositions are useful for treating or preventing infections by filoviridae. In another embodiment, the compounds and compositions are useful for treating or preventing infections by cuevavirus, Ebola virus, or Marburg virus. In another embodiment, the compounds and compositions are useful for treating or preventing infections by poxviridae. In another embodiment, the compounds and compositions are useful for treating or preventing infections by orthopoxvirus. In another embodiment, the compounds and compositions are useful for treating or preventing infections by vaccinia virus.

In another embodiment, the compounds and compositions are useful for treating or preventing infections by HSV, Ebola virus or vaccinia. In another embodiment, the compounds and compositions are useful for treating or preventing infections by HSV virus. In another embodiment, the compounds and compositions are useful for treating or preventing infections by Ebola virus. In another embodiment, the compounds and compositions are useful for treating or preventing infections by vaccinia.

In one embodiment, the disclosure provides a method of treating a subject infected with herpes simplex virus, Ebola virus or vaccinia, the method comprising administering to the subject a compound of formula (I) as defined herein, or a pharmaceutical composition as described herein in an amount to treat infection by the herpes simplex virus, Ebola virus or vaccinia in the subject.

In one embodiment, the method of treating a subject infected with herpes simplex virus, Ebola virus or vaccinia further comprises administered a second therapeutic agent. As described above, the second therapeutic agent includes those that are known and those discovered to be effective in the treatment of HSV, Ebola viral or vaccinia infections. The compound described herein and the second therapeutic agent may be administered simultaneously in either the same or different pharmaceutical composition or sequentially in any order. The amounts of compound described herein and the second therapeutic agent and the relative timings of their administration will be selected to achieve the desired combined effect.

Any compound or pharmaceutical composition described herein may be used in the methods of the present disclosure.

In some of the above methods, the compound described herein is administered to a subject in a composition comprising a pharmaceutically acceptable carrier. In some of these embodiments, the composition is administered intravenously. In certain embodiments, the compound is formulated in a unit dosage injectable form. In some of embodiments, the composition is formulated for topical administration, such as a lotion or a cream.

In preferred embodiments of each of the above methods, the subject is a human. In other preferred embodiments, the subject is an animal.

In an additional embodiment, the present disclosure provides the use of a compound of described herein in the manufacture of a medicament for the treatment of an infection by HSV, Ebola virus or vaccinia. It will be appreciated that a compound described herein and one or more second therapeutic agents may be used in the manufacture of the medicament.

In additional embodiments, the present disclosure provides a kit comprising a compound described herein, a container, and a package insert or label indicating that the compound can be used to treat an infection by HSV, Ebola virus or vaccinia.

The term "package insert" is used to refer to instructions customarily included in commercial packages of therapeutic products that contain information about the indication(s), usage, dosage, administration, contraindications and/or warnings concerning the use of such therapeutic products.

In order that this invention be more fully understood, the following examples are set forth. These examples are for the purpose of illustration only, are applicable to one or more embodiments and are not to be construed as limiting the scope of the invention in any way.

EXAMPLES

This research tested a variety of inorganic ions, both cations and anions, that may form complexes with caffeic acid and related compounds. The main tests included 1) testing caffeic acid paired with a variety of both anions and cations, 2) determining the toxicity levels of selected caffeic acid-inorganic complexes to calculate a selectivity index; 3) evaluating different molar ratios of selected inorganic compounds with caffeic acid; 4) testing the most active complexes against various virus families; and 5) determining the activity of other structurally-related compounds when paired with a select group of inorganic compounds to identify which properties of the molecule were the most important in imparting antiviral activity.

Example 1. Preparation of Caffeic Acid Chelates

The preparation of the organic-inorganic complexes followed the same protocol for all the tests unless otherwise noted. All the organic and inorganic reactants were purchased from Sigma-Aldrich. The cationic species were purchased as chloride salts (e.g. $FeCl_3.6H_2O$) while the anionic species were purchased as sodium salts (e.g. $Na_3PO_4.12H_2O$). For each organic compound of the disclosure tested, a desired mass of the compound was weighed out with an accuracy of 0.1 mg and dissolved in methanol to create a stock solution. The desired molar ratio of the organic to inorganic compound was 2:1, which would allow for two molecules of the organic to chelate the same ion as Hider et al [17] suggested for catechol-containing molecules chelating iron(III) at pH 7. If only a single organic molecule chelates an ion, then there would be an excess of the organic compound. The inorganic compounds were dissolved in 18 MΩ water to make a stock solution. The individual organic-inorganic complexes were created by adding the organic chemical dissolved in the methanol to the inorganic chemical dissolved in water and allowing the chemicals to react for 24 hours at room temperature (22° C.). The samples were then dried with air to obtain a solid material that could subsequently be resuspended and used for antiviral testing.

Two tests deviated from this standard protocol. The first test was the evaluation of different molar ratios of the inorganic compounds to the organic compounds. In this case, the most promising pairings of caffeic acid and inorganics, including iron(III), phosphate and molybdate, were tested with different molar ratios, namely 0, 0.1, 0.25, 0.5, 1.0 and 2.0, of the inorganic to the organic compound. Multiple catechol-containing molecules can chelate a single cation[17], so the test of different molar ratios of the caffeic acid to the cation investigates that possibility of different ratios of cation to chelate. Three different concentrations (16.7, 56.7 and 167 μM) of each permutation of chemical and molar ratio were conducted to estimate the viral 50% inhibitory concentration ($IC_{50}$) for each molar ratio. Upon preparing the samples, some of the samples formed precipitates in the stock solutions that could not be re-dissolved for the antiviral assay and were omitted from analysis. The second test that deviated from the typical sample preparation was the "ions only" control when the inorganic chemicals were tested in the absence of any organic compound (e.g.

caffeic acid) to determine the degree of antiviral activity due to the inorganic ions alone. In this case, the sample preparation was the same, but pure methanol was mixed with the inorganic stock solution. The samples were subsequently processed in the same fashion as the normal samples, namely they reacted for 24 hours at room temperature and then were dried to a solid with air.

Example 2. Antiviral Activity Assays

The antiviral assays were conducted as follows. For HSV1 and HSV2, Vero cells were grown in Dulbecco's minimal essential media containing 10% heat inactivated fetal bovine serum and antibiotic/antimycotic (ThermoFisher) in a 37° C., 5% $CO_2$ incubator. Cells were seeded in standard 6-well tissue culture dishes. HSV1 virus was diluted to 100 plaque forming units/100 µL complete media. The virus samples were treated for 15 minutes with the indicated concentrations of the test compound/material. These treated viral samples were used to infect the confluent Vero cell monolayers. Cells were infected for 1 hour at 37° C. with occasional rocking. After 1 hour, 2 mLs of complete media was added to each well. The test compound was added to the media at the indicated concentration. The dishes were placed in the incubator for 3 days. After 3 days, the media was removed and the cells stained with 0.5% crystal violet. The number of plaques present were counted by hand and graphed as a percent relative to untreated samples.

Similar assays were done for other viruses. For vaccinia virus (Copenhagen strain), Vero cells were used and plaques visualized after 3 days; for Rhinovirus 14, Hela-H1 cells were used, grown at 33° C. in the above complete media plus glutamine, and plaques visualized after 4 days; for Zika virus, Vero cells were used and plaques visualized after 4 days; for reovirus type 3, Hela cells were used, overlaid with complete media containing 0.5% agarose and plaques visualized after 5 days; for encephalomyocarditis virus (EMCV), Hela cells were used, overlaid with complete media containing 0.5% agarose and plaques visualized after 2 days; for vesicular stomatitis virus (VSV), Vero cells were used, overlaid with complete media containing methylcellulose and plaques visualized after 2 days; and for VSV-Ebola pseudotype (kindly provided by Dr. Thomas Geisbert, University of Texas Medical Branch), Vero cells were used, overlaid with complete media containing methycellulose and plaques visualized after 4 days.

Example 3. Cellular Toxicity Assays

Vero cells grown in complete media were treated with varying concentrations of the indicated concentrations of the test compound. Twenty-four hours post treatment, the cell monolayers were released in trypsin, and the resuspended cells treated with 0.2% trypan blue solution (HyClone). The number of stained cells and total number of cells were counted using a hemocytometer and the percentage of viable cells calculated.

Results

Our previous research of extracts of M. officinalis demonstrated not only the presence of multiple organic acids with the caffeoyl moiety, but also showed relatively high concentrations of iron, zinc and copper as determined by x-ray fluorescence methodologies. These partly purified M. officinalis extracts contained sufficient metals to obscure all compounds from NMR analysis even after multiple organic solvent exchanges and extractions that would have left any ionic materials behind. Caffeic acid and related compounds contain a catechol functional group, which is a well-known metal chelation functional group[15, 20]. Other groups have shown that the chelation of a metal enhances, or is essential, to the antioxidant activity of caffeic acid compounds[21]. However, the role of metal chelation by caffeic acid in regard to the potential antiviral activity has never been reported. Prior antiviral studies that investigated these compounds typically used cell culture media that often contain iron, so metal chelation may have occurred even if no additional metal was present. The goal of this study was to evaluate the importance of ionic metals and anionic inorganic molecules in regard to antiviral activities of caffeic acid and related compounds towards HSV1 and other viruses.

Caffeic Acid Paired with Different Ionic Substances

The first test was to compare the activity of caffeic acid when paired with a range of both anionic and cationic inorganic compounds (FIG. 1). The results showed that the majority of the inorganic ions tested enhanced the anti-HSV1 activity of caffeic acid with increases upwards of 100-fold. Of the cationic substances, iron(III) was the most active ($EC_{50}=37$ µM) followed by copper(II) with an $EC_{50}$ of 117 µM. Zinc yielded only minimal improvements with an EC50 of 3,720 µM. In contrast, the $EC_{50}$ of caffeic acid alone averaged 18,600 µM from two separate tests. All cations tested showed statistically higher antiviral activity ($p<0.05$; probit analysis with Wald's chi-square test) except for zinc.

The high degree of activity of iron(III) is advantageous from an application point of view since iron is an essential nutrient with almost no toxicological hazards; thus, it would be very safe to include in a pharmaceutical formulation. Prior research has shown that dihydrocaffeic acid can form complexes with iron(III), and the chloride salts of iron(III) in particular [22], so similar complexes are expected with caffeic acid as well. Catechol functional groups, such as that in caffeic acid, tend to favor chelation of tribasic cations like $Fe^{3+}$ and $Al^{3+}$, [17] which may explain the greater activity of iron(III) compared to all the other +2 cations tested. This is a tight chelation even at pH 7, which is the most biologically relevant condition.

The anionic complexes of caffeic acid (FIG. 1) likewise showed mixed results. In this case, the molybdate ion ($MoO_4^{2-}$) was the most effective ($EIC_{50}=54$ µM) followed by tungstate ($WO_4^{2-}$, 77 µM). Phosphate had lower activity (584 µM) and sulfate showed no increased activity over caffeic acid alone. All anions tested showed statistically higher antiviral activity ($p<0.05$; probit analysis with Wald's chi-square test) except for sulfate. Since the cell culture system was buffered at pH 7.1, the phosphate was probably present as a mixture of $HPO_4^{2-}$ and $H_2PO_4-$, while the molybdate, tungstate and sulfate were almost exclusively in the $-2$ charge state. In terms of pharmaceutical formulations, phosphate is very abundant in biological systems and would be expected to have effectively no toxicity on its own. Molybdate is rare in biological systems, but it is the core of the molybdenum cofactor (often called MOCO) that is used in some enzyme systems [23]. However, adding large amounts of molybdate to a biological system may have unwanted side effects. Little is known about the biological fate of tungstate, but it has been recently suggested that it also may be incorporated into selected enzymes in a similar fashion as molybdate to which it is closely related.

Figure 2:
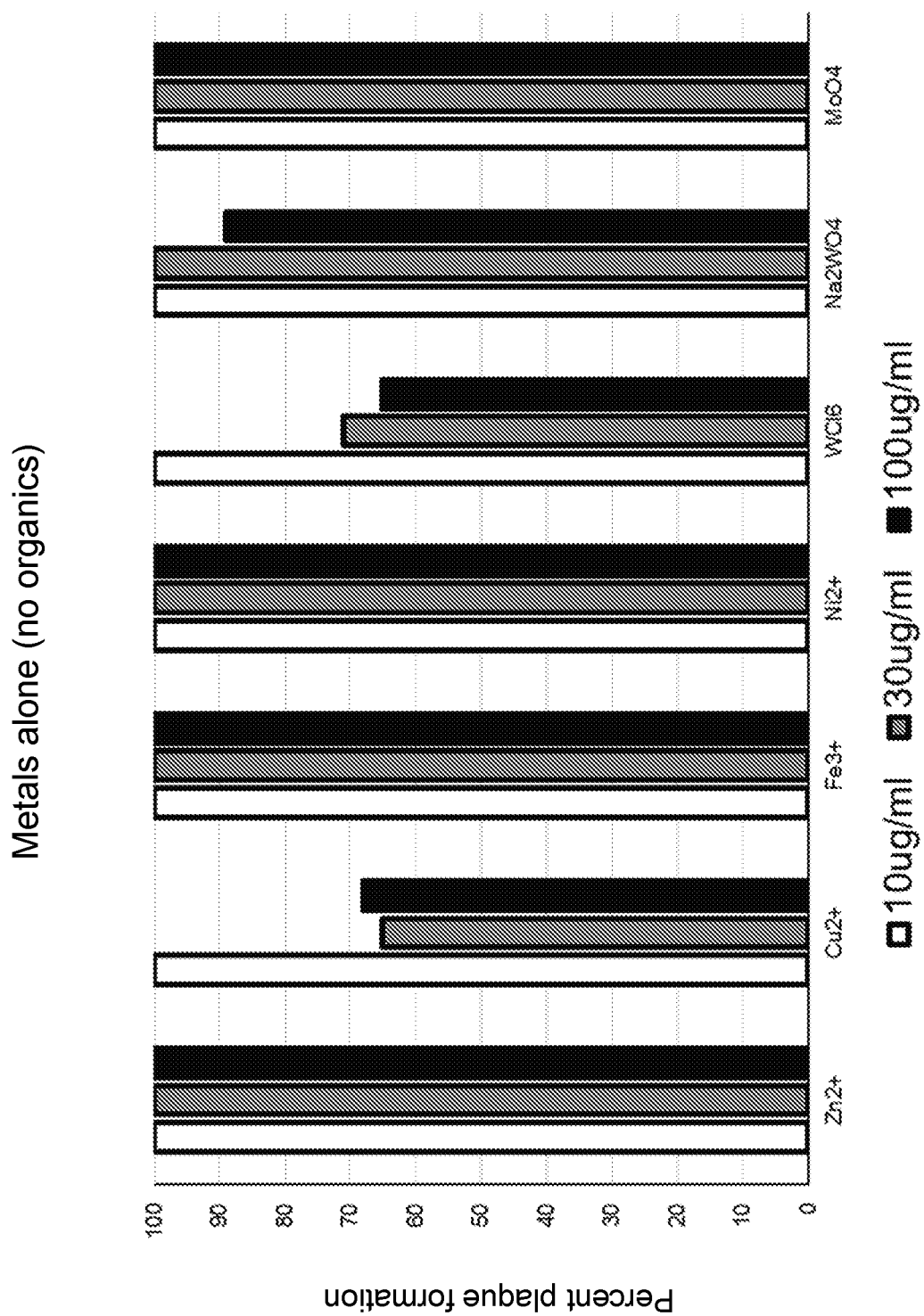
FIG. 2 and FIG. 3 show the lack of antiviral activity of the inorganic ions in the absence of caffeic acid.

The inorganic ions were tested in the absence of caffeic acid to ensure the observed activity in the prior tests was due to a caffeic acid-inorganic complex rather than the metals by themselves. None of the inorganic compounds had any observable inhibition at 83 μM, which was the highest dose tested, except for copper(II) that had a 38% inhibition of plaque formation (FIG. 2 and FIG. 3). This indicates that a large fraction of the activity of the caffeic acid with copper (II) test could be the result of free copper ions. However, the other inorganic compounds had no activity at the concentrations tested supporting that the observed activity must be the result of a caffeic acid-inorganic complex.

Acyclovir was included in the test as a positive control to ensure the assay is functioning properly. It also provides a benchmark for comparison. In this trial, acyclovir was about 20-fold more active than the caffeic acid and iron chelates.

Varying Molar Ratios of Selected Inorganic Compounds with Caffeic Acid

Figure 4:
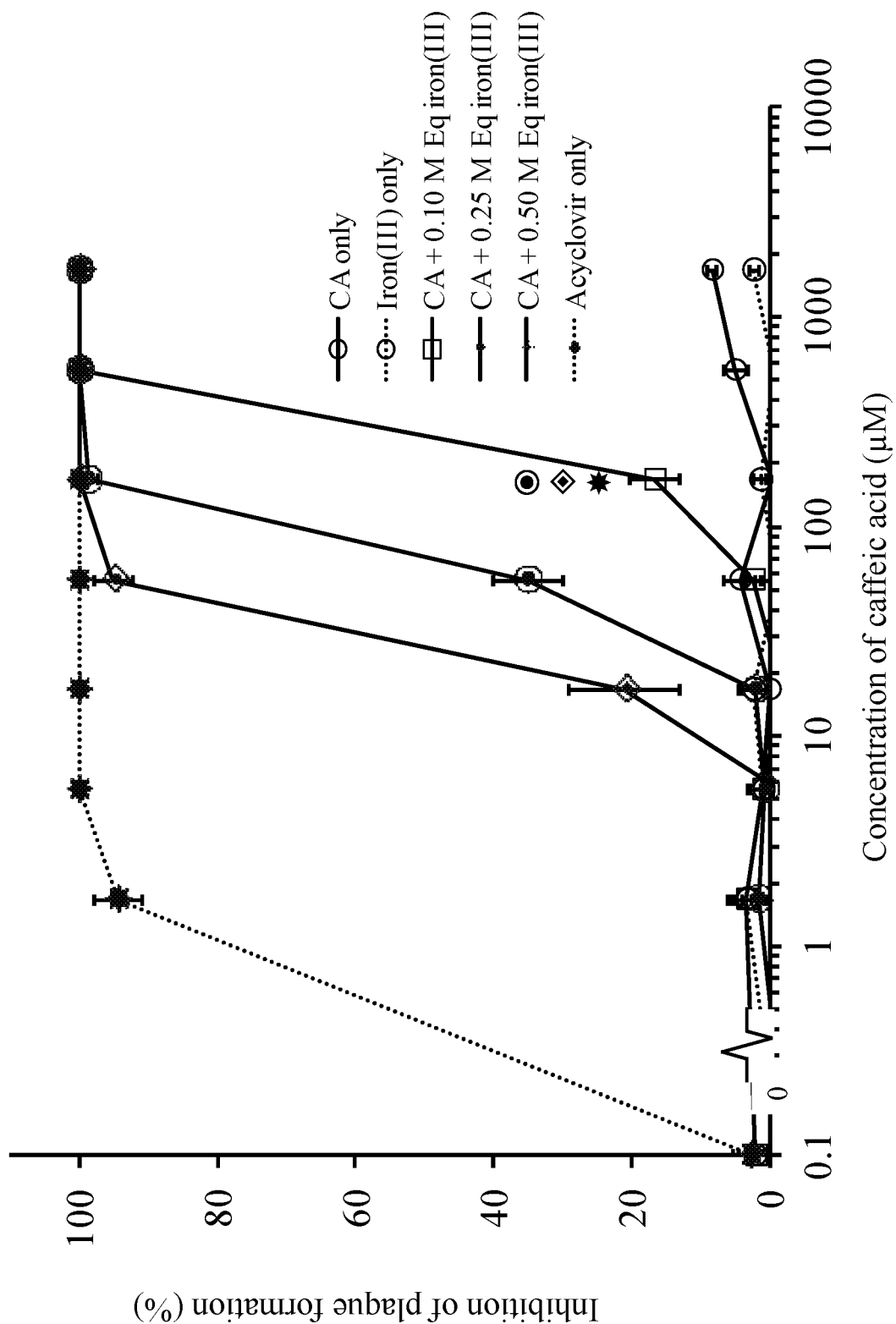
FIG. 4 shows inhibition of plaque formation (mean % relative to controls±standard error, n=3 per point) of caffeic acid (CA) combined with different molar ratios of iron(III) chloride. The "iron(III) only" test used the same amount of iron as the 0.5 M Eq of caffeic acid test and is plotted as if it were the same caffeic acid concentration for direct comparisons between the iron only and the "caffeic acid+0.5 M Eq iron(III)" test. Acyclovir is included as a positive control and a benchmark performance standard.

The first series of tests (FIG. 1) used a 2:1 molar ratio of the organic compound to the inorganic compound so that two organic molecules could chelate one ionic molecule. Subsequently, tests were conducted to determine whether a different molar ratio would be optimal. The results (FIG. 4) showed that increasing the molar ratio of the inorganic produced increasing anti-HSV1 activity up to the point precipitates began to form during preparation of the concentrated stock solution (28,000 μM caffeic acid) from which the aliquots for testing were taken. However, the largest improvement in activity occurred when increasing from the "no ions" control to the 0.1 molar ratio ($EC_{50}$=163 μM), which suggests that even small amounts of ions can have a relatively large impact of the anti-HSV1 activity of caffeic acid. Increasing the iron ratio to 0.25 and 0.5 molar equivalents produced incremental improvements with EC50 values of 55 and 27 μM, respectively. Iron(III) by itself had no detectable antiviral activity. All the treatment groups are statistically different from each other ($p<0.05$) as conducted by a probit analysis followed by a large-sample Wald's chi-square test to determine differences between slopes and intercepts.

The preceding calculations were conducted on the basis of the concentration of caffeic acid, but if the calculations are conducted on the concentration of iron rather than caffeic acid, then a rather different result is obtained. The EC50 for the 0.1, 0.25 and 0.5 M Eq tests are 16.3, 13.8 and 13.3 μM of iron(III), respectively, which are remarkably similar. Therefore, it would appear that the amount of iron is driving the antiviral activity of the chelate and the caffeic acid is present in excess in these three tests. It is worth noting that the cell culture media has a trace amount of iron present since iron is essential for cell growth. Therefore the "no ions" control still has a trace of iron in the cell culture, but this is assumed to be an appropriate concentration for living tissues. The experiment here shows that adding additional iron chelated to caffeic acid will have additional activity above the ambient levels found in tissues.

Cellular Toxicity of Caffeic Acid Paired with Selected Ionic Substances

Figure 5:
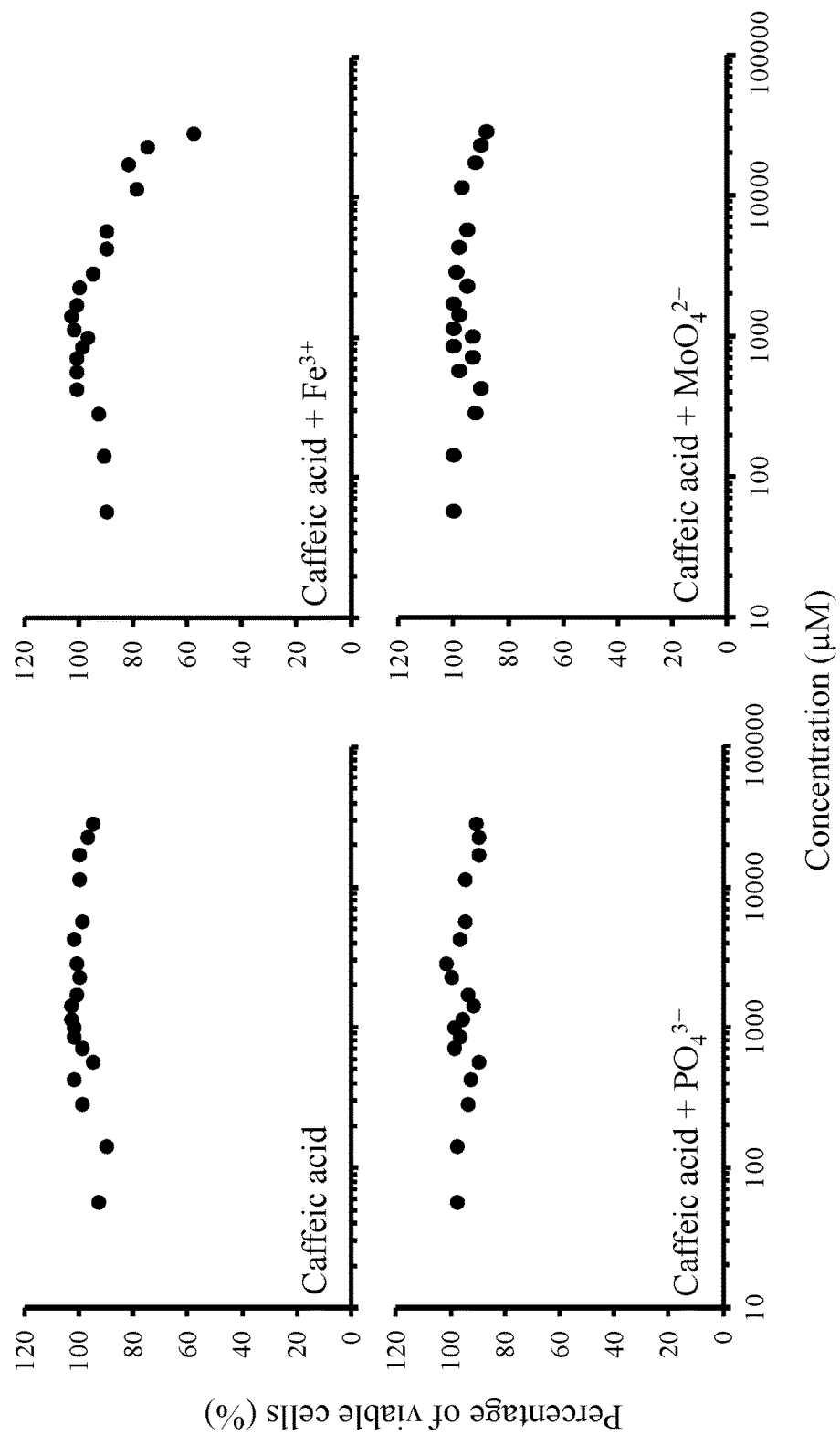
FIG. 5 shows the cellular toxicity of caffeic acid and combinations of caffeic acid and $Fe^{3+}$, $MoO_4^{2-}$ or $PO_4^{3-}$.

The next aspect of this research was to determine potential cellular toxicity effects of caffeic acid and selected inorganic compounds. For this test, the treatment included caffeic acid alone, caffeic acid+iron(III); caffeic acid+molybdate, and caffeic acid+phosphate. Iron and molybdate were chosen since they were the most active cation and anion when paired with caffeic acid. Phosphate was chosen as the last ion simply because of its biological prevalence and presumed low toxicity. The results (FIG. 5) showed no toxic effect (cell viability 90% or above) for either caffeic acid or caffeic acid+$PO_4^{3-}$ even at the highest concentrations tested, namely 27,000 μM. Caffeic acid paired with molybdate showed only very minor toxicity (88% cell viability) at the highest concentration tested. Surprisingly, the caffeic acid+$Fe^{3+}$ showed the highest toxicity with toxic effects beginning at 11,000 μM and the cell viability dropping to 58% at the highest tested concentration of 27,000 μM. The iron(III) chloride that was used to make these solutions is a fairly acidic chemical acting as a Lewis acid, so some of the observed effects at high concentration may have been the result of excessive acid overwhelming the buffer in the cell culture. For the caffeic acid+$Fe^{3+}$ test, the selectivity index (SI) is approximately 745. Since there was insufficient cellular toxicity in the other tests to obtain a 50% toxicity ($TD_{50}$) value, a selectivity index (SI) can only be estimated using the highest concentration tested, which will result in a lower limit of the SI. When this calculation was conducted, the SI for caffeic acid with molybdate was >519 and caffeic acid with phosphate was >48. The differences between these three samples lie only in the differences in the $EC_{50}$ concentrations. On a cellular level, these data suggested that these metal chelates have a wide safety margin.

Antiviral Activity Towards Other Virus Strains

Figure 6:
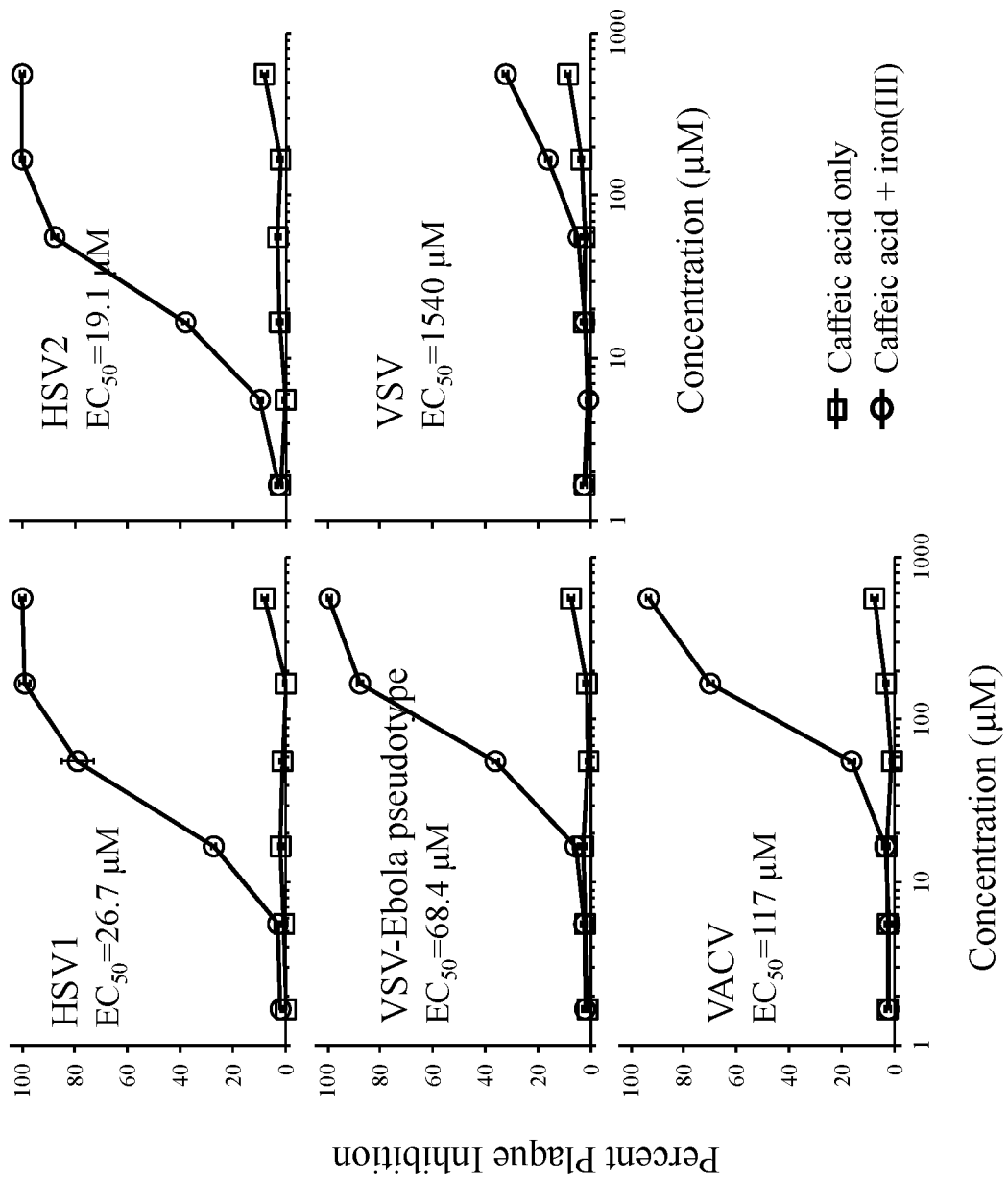
FIG. 6 shows inhibition of plaque formation (mean % relative to controls±standard error, n=3 per point) of caffeic acid and caffeic acid-iron(III) chelate towards various viruses. The $EC_{50}$ values reported are the $EC_{50}$ of the caffeic acid-iron(III) chelate. Zika virus, Rhinovirus and Reovirus were also tested and found to be unaffected by caffeic acid or the caffeic acid-iron(III) complex.

Based on the anti-HSV1 activity of the caffeic acid metal complexes, the best metal complex, namely caffeic acid with 0.5 M equivalent iron(III), was tested against other viruses, including non-related virus families (FIG. 6). The results of this test showed that the herpes simplex viruses were the most affected by the caffeic acid-iron(III) chelate with HSV1 having an EC50=26.7 μM in this test and HSV2 having an $EC_{50}$=19.1 μM. The caffeic acid chelates also showed antiviral activity against the VSV-Ebola pseudotyped virus ($EC_{50}$=68.4 μM) and vaccinia virus ($EC_{50}$=117 μM). The caffeic acid chelates showed only minor activity towards the wild type vesicular stomatitis virus (VSV) with an $EC_{50}$ of 1540 μM (extrapolated from dose-response curve). Caffeic acid by itself had minimal effect on the viruses test (FIG. 6). All the viruses tested were significantly different from each other ($p<0.05$; probit analysis with Wald's chi-square test). The caffeic acid-iron chelate was tested against Zika virus, Rhinovirus and Reovirus but these viruses were unaffected at the concentrations tested.

These results support our previous studies investigating the antiviral activity of *M. officinalis* where vaccinia virus had similar sensitivity as HSV1 to *M. officinalis* extracts (10). The inhibitory activity of *M. officinalis* towards HSV1 targets the virion gB thereby preventing interaction with heparan sulfate proteoglycans on the cell surface. Vaccinia virus infection can by inhibited by soluble heparan sulfate (24), in agreement with the ability of *M. officinalis* to inhibit infection. In addition, published data on filoviruses, including Ebola virus, states that viral attachment to cells requires binding to cellular heparan sulfate proteoglycans (25). Based on this similarity to HSV1 and vaccinia virus, we wanted to test if the caffeic acid chelates would be able to inhibit Ebola virus infection. Since wild-type Ebola virus requires a Biosafety Level 4 facility, VSV-Ebola pseudotype was obtained in which the VSV surface glycoprotein (G) has been replaced with the Zaire Ebola virus glycoprotein (GP). This virus will utilize cell attachment mechanisms of Ebola, but is non-virulent due to the VSV core. As shown, this VSV-Ebola pseudotype virus was sensitive to the antiviral activity of the caffeic acid chelates. The other viruses tested, including VSV, have not been shown to require heparan sulfate proteoglycans for cellular attachment and were insensitive to treatment with caffeic acid chelates. The previous studies on *M. officinalis* along with our current results support that caffeic acid chelates are likely targeting viral attachment to the cell by preventing interaction with the cellular heparan sulfate or related receptors.

Anti-HSV1 Activity of Additional Compounds of the Disclosure

Figure 7:
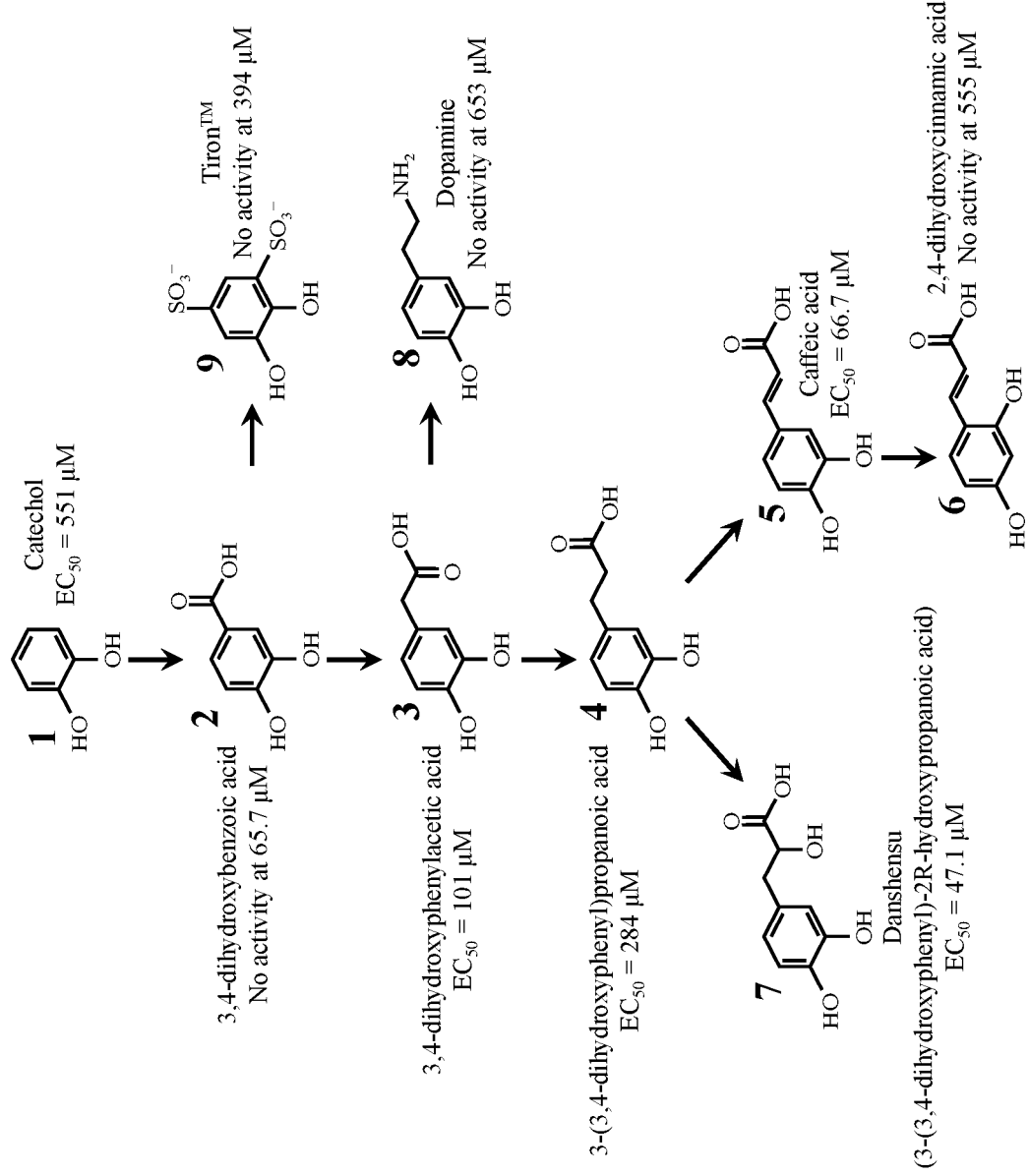
FIG. 7 shows HSV1 $EC_{50}$ values for additional compounds of the present disclosure when combined with iron (III). Test compounds labeled as "no activity" indicate that no activity was detected for that compound and the value given afterward was the highest concentration tested. The HSV1 $EC_{50}$ for these test compounds would be far greater than the "no activity" level. Each arrow represents a single modification to the molecule except #9 that replaced a carboxylic acid with two sulfonic acids. Each $EC_{50}$ value was determined from a single dose-response trial with a minimum of three test concentrations.
Figure 8:
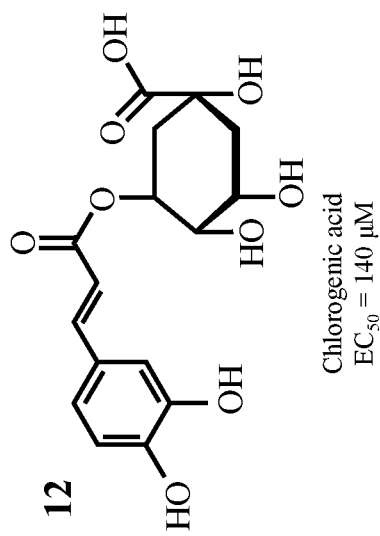
FIG. 8 shows the activity of additional compounds of the present disclosure. The HSV1 $EC_{50}$ values are for test compounds when combined with iron(III). Nordihydroguaiaretic acid had no activity at 330 μM, so this compound was effectively inactive. Each $EC_{50}$ value was determined from a single dose-response trial with a minimum of three test concentrations.
Figure 8:
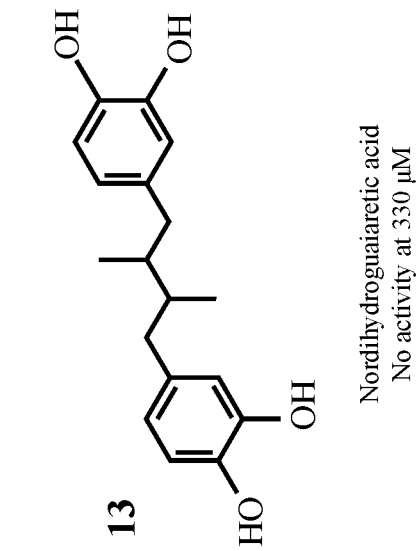
Figure 8:
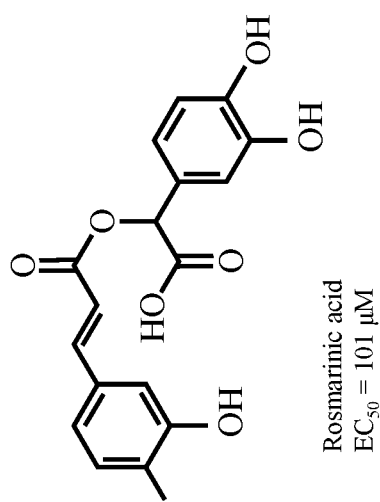
Figure 8:
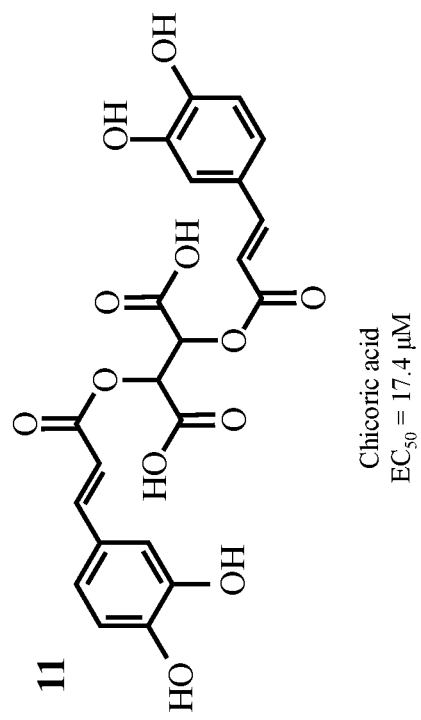
Figure 9:
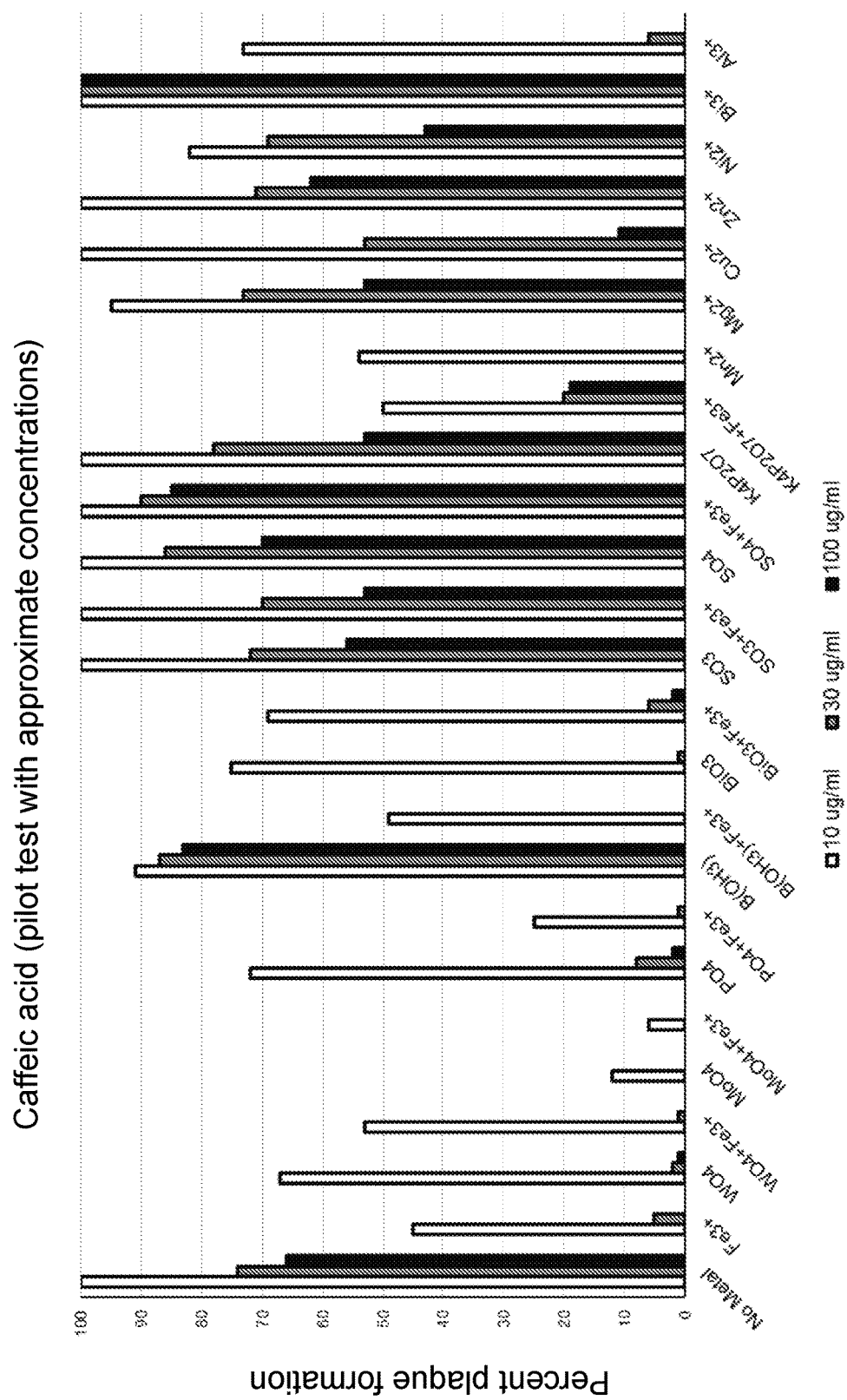
FIG. 9 shows the anti-herpes-simplex-virus (HSV) activity of caffeic acid with a variety of both cation and anions at different concentrations.
Figure 10:
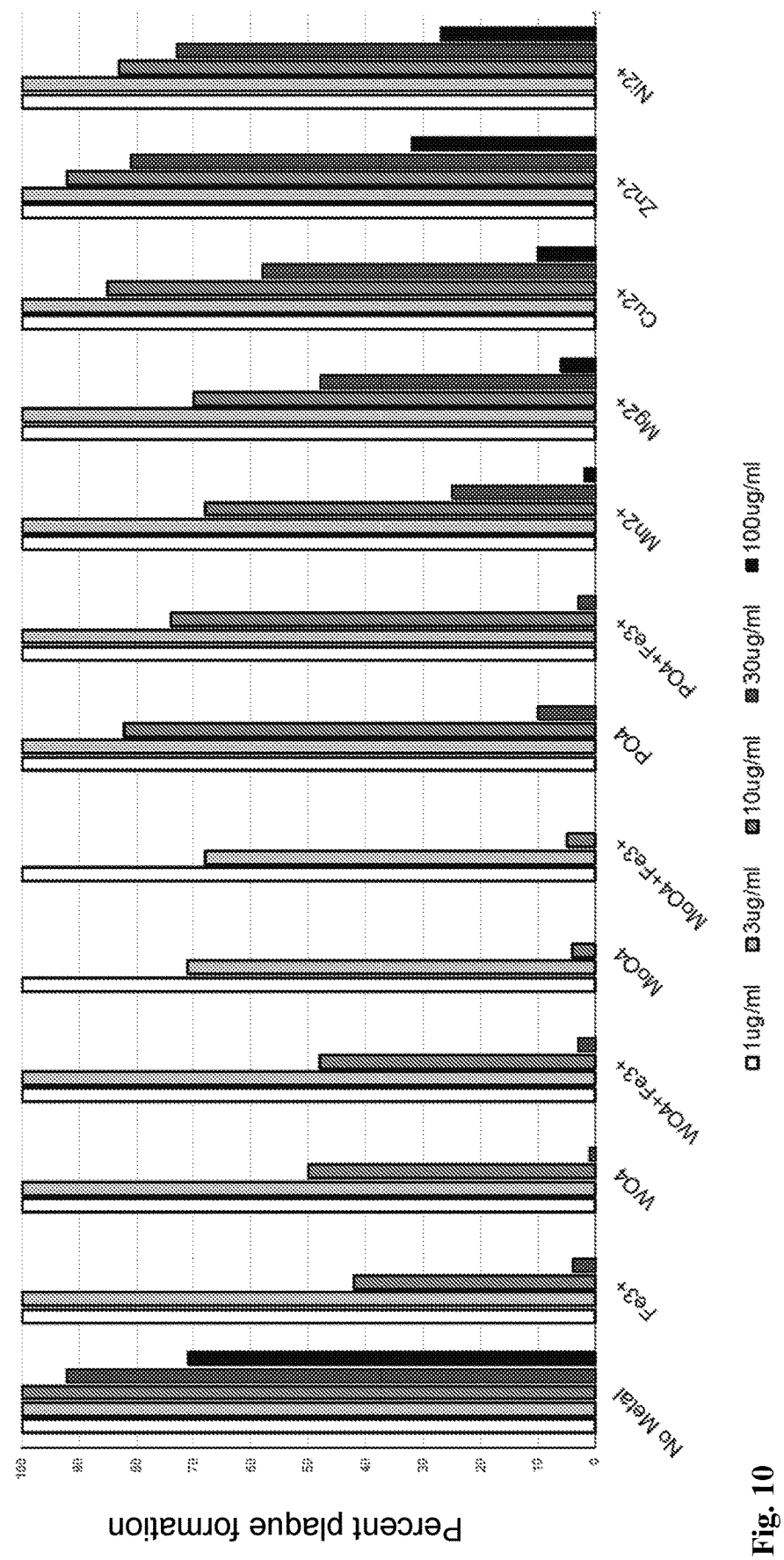
FIG. 10 shows the anti-herpes-simplex-virus (HSV) activity of caffeic acid with a variety of both cation and anions at different concentrations.

Additional compounds of the present disclosure were tested to determine which aspects of the molecule are important for the antiviral properties when paired with inorganic ions (FIG. 7 and FIG. 8). For this analysis, $Fe^{3+}$ was chosen as the preferred ion for the comparisons since is showed the greatest promise of the cations in the prior tests. The most active compounds, as determined by the HSV1 $IC_{50}$ values, were: chicoric acid (17.4 μM), Danshensu (47.1 μM, AKA 3-(3,4-dihydroxyphenyl)-2-hydroxypropanoic acid), caffeic acid (66.7 μM in this batch of samples), 3,4-dihydroxylphenylacetic acid (101 μM) and rosmarinic acid (101 μM). This series of compounds revealed some characteristics that are required for the iron chelate to have antiviral activities. First, the compound must have a catechol functional group as evidenced by the inactivity of 2,4-dihydroxycinnamic acid (6) compare to caffeic acid (5, which is also called 3,4-dihydroxycinnamic acid). Catechols are known metal chelators [15-19], so this was expected. However, the presence of a catechol group was not sufficient for anti-HSV1 activity as determined by the low activity of catechol (1), Tiron™ (9), dopamine (8), 3,4-dihydroxybenzoic acid (2) and Nordihydroguaiaretic acid (13). Effective compounds also require a carboxylic acid functional group a particular distance away from the catechol as exemplified by comparing compounds 1 to 4. An amine functional group, which is also expected to be ionized at pH 7.1, was not an effective substitute for a carboxylic acid group as evidenced by the difference between compounds 3 and 8. The presence of an unsaturation or hydroxylation in the carbon chain attached to the aromatic also seems to improve anti-HSV 1 activity.

Larger molecules that contain a caffeoyl moiety were likewise active when paired with $Fe^{3+}$ so long as the compound had at least one carboxylic acid on/near the substituted side chain (FIG. 8). Chicoric acid had two caffeoyl groups and two carboxylic acids in nearby positions, so it is not surprising that its activity was a little over triple that of caffeic acid alone when the results were calculated on a molar basis. Rosmarinic acid, which had one caffeoyl moiety and one acid, had similar molar activity as caffeic acid. The one larger compound tested, nordihydroguaiaretic acid, had two catechol groups but no carboxylic acids (13) had no anti-HSV1 activity.

Discussion

Caffeic acid and compounds with caffeoyl functional groups have been known to be antiviral towards both HSV1 and HIV[5, 12, 13]. However, this is the first time that the addition of a metal ion (cationic or anionic) has been shown to enhance or be essential to the antiviral activity of these compounds upwards of 100-fold. This observation provides additional information about the active form of the chemical that was lacking before, namely that the organic compounds are apparently in a complex with a metal and that the metal complex is the actual active compound. Prior studies, and the "no ions" control in this study, have shown that the organic compounds have some low activity on their own. However, this might be the result of unanticipated chelation occurring with the trace amount of iron that is typically present in cell culture media to ensure the healthy growth of cells. The cell culture media utilized in this research had an iron(III) concentration of 0.25 μM even without any iron being added. However, this amount is about 50 times smaller than the amount of iron needed to generate an EC50 value in the caffeic acid test.

Previous studies using botanical extracts, including *M. officinalis*, has suggested a role of compounds with caffeoyl functional groups as being the active antiviral constituents present in these extracts. Indeed, antiviral extracts of *M. officinalis* are known to contain high levels of rosmarinic acid which is suggested to be the main contributor of the antiviral activity [4, 26]. However, the requirement of ionic metals and anionic inorganic molecules in regard to the antiviral activities of rosmarinic acid in *M. officinalis* has never been evaluated. As discussed above, compounds with caffeoyl functional groups isolated from *M. officinalis* would likely be associated with ionic metals and anionic inorganic molecules. When our group previously attempted to purify the active constituent(s) present in *M. officinalis* extracts, the partly purified preparations contained detectable amounts of iron, copper and zinc as determined by x-ray fluorescence even after multiple organic solvent exchanges and extractions that would have left any ionic materials behind.

Most of the structural activity relationships for these compounds, and chicoric acid in particular, has been conducted on HIV-1 integrase (12, 13). HIV-1 integrase is an intracellular process that is completely different from the extracellular HSV1 viron attachment process of cellular heparan sulfate proteoglycan binding that appears to be the mechanism of action in this study. Given the same type of molecule is effective in both situations, it is still advantageous to compare the structural activity relationships to provide possible avenues for research into both mechanisms. For HIV-1 integrase inhibition, the catechol functional groups were not essential so long as they were converted to acetate esters (12), so a future test with caffeic acid would be to convert the caetchols to acetate esters and then determine the activity. However, methylation of the catechols eliminated all antiviral inhibition. (12, 13) Lin et al (12) also showed that the presence of Mn2+ had no effect on HIV-1 integrase inhibition while Mg2+ actually reduced inhibition activity of chicoric acid. In this case, divalent metal chelation did not increase activity.

The studies conducted here were tissue culture studies, so the pharmacokinetics of these metal chelates is largely unknown. Since the compounds are often ionic at physiological pH, it is expected that they may be removed from the body relatively fast via a urinary route. The larger compounds that contain a caffeoyl moiety (chicoric, rosmarinic and chlorogenic acids) are all vulnerable to carboxylester hydrolysis, which is a limitation of these compounds for pharmaceutical use (13). The result of hydrolysis is the liberation of caffeic acid, which further argues for the use of caffeic acid to start with rather than a more expensive larger molecule. There may be concerns with adding metal ions to the biological system that might precipitate in the body, but the presence of the chelation agent reduces this possibility. One potential application of these compounds may be topical creams to treat open sores and thus bypass the problems associated with distribution of the chemical through the body and possible metabolism and elimination.

The active form of the chemical is believed to be a caffeic acid chelate, although we were unable to conclusively prove the structure of this complex. However, there is ample evidence that the active form is a chelate. The first piece of evidence is that catechol functional groups, such as those in caffeic acid, are known metal chelators (15-19), so chelation is expected in these molecules. Second, iron(III) by itself had no antiviral properties and caffeic acid had weak antiviral properties, but the mixture increased the antiviral activity by about 100-fold, which shows an effect far greater than additive effects of the two components. The optical absorption at 600 nm for the caffeic acid (50 μg/mL) and iron(III) chloride (45 μg/mL) solutions were 0.000 and 0.005 Abs, respectively. However, a solution created with both the chemicals at the same concentrations as the individual solutions had an absorbance of 0.145 Abs, which shows a 29-fold increase in absorption was created by combining the mixtures. Fourth, the solubility of the caffeic acid/iron(III) mixture has low solubility in acidic water (pH<4), but they become soluble in neutral and basic solutions. This is probably due to the ionization of the carboxylic acid functional group on caffeic acid, which demonstrates that acid functional group is still available. The implication is that the association between the iron and the caffeic acid is occurring at the catechol functional group as expected. Unfortunately, attempts to crystallize the chelate complex were unsuccessful in a variety of solvent mixtures, so the definitive x-ray crystallography structural elucidation could not be conducted. Ultimately, the exact structure of the caffeic acid-iron complex is largely academic since the mixture was proven to be effective against HSV viruses.

The primary conclusions of this research were that the anti-HSV activity of compounds with caffeoyl functional groups can be enhanced over 100-fold by the addition of relatively innocuous iron(III) ions. The mechanism of action appears to be an inhibition of viron binding to the cells, which is different than the intracellular mechanism of acyclovir. This suggests that acyclovir and the caffeic acid chelates could be administered together to obtain greater virus control without encountering toxicity issues associated with simply increasing the dose of acyclovir. Lastly, the cellular toxicity of the chelates is very low and organism-level toxicity is expected to be low based on the common and innocuous nature of the components of the chelates. Future research should focus on testing mixtures of caffeic acid chelates with acyclovir and other current use antiviral agents to determine if the effects are additive. Additionally, the caffeic acid chelates need to be tested in animal models for both effectiveness and pharmacokinetic properties.

REFERENCES

The following references are hereby incorporated by reference in their entireties:
1. Astani A, Navid M H, Schnitzler P. Attachment and Penetration of Acyclovir-resistant Herpes Simplex Virus are Inhibited by *Melissa officinalis* Extract. Phytotherapy Research. 2014; 28(10):1547-52. doi: 10.1002/ptr.5166. PubMed PMID: WOS:000342798700016.
2. Petersen M, Simmonds M S J. Molecules of interest—Rosmarinic acid. Phytochemistry. 2003; 62(2): 121-5. doi: 10.1016/s0031-9422(02)00513-7. PubMed PMID: WOS:000180951600001.
3. Swarup V, Ghosh J, Ghosh S, Saxena A, Basu A. Antiviral and anti-inflammatory effects of rosmarinic acid in an experimental murine model of Japanese encephalitis. Antimicrobial Agents and Chemotherapy. 2007; 51(9): 3367-70. doi: 10.1128/aac.00041-07. PubMed PMID: WOS:000249175400048.
4. Astani A, Reichling J, Schnitzler P. *Melissa officinalis* Extract Inhibits Attachment of Herpes Simplex Virus in vitro. Chemotherapy. 2012; 58(1):70-7. doi: 10.1159/000335590. PubMed PMID: WOS:000301625200009.
5. King P J, Ma G X, Miao W F, Jia Q, McDougall B R, Reinecke M G, et al. Structure-activity relationships: Analogues of the dicaffeoylquinic and dicaffeoyltartaric acids as potent inhibitors of human immunodeficiency virus type 1 integrase and replication. Journal of Medicinal Chemistry. 1999; 42(3):497-509. doi: 10.1021/jm9804735. PubMed PMID: WOS:000078602600019.
6. Louvel S, Moodley N, Seibert I, Steenkamp P, Nthambeleni R, Vidal V, et al. Identification of compounds from the plant species *Alepidea amatymbica* active against HIV. South African Journal of Botany. 2013; 86:9-14. doi: 10.1016/j.sajb.2013.01.009. PubMed PMID: WOS: 000318055800003.
7. Tewtrakul S, Miyashiro H, Nakamura N, Hattori M, Kawahata T, Otake T, et al. HIV-1 integrase inhibitory substances from *Coleus parvifolius*. Phytotherapy Research. 2003; 17(3):232-9. doi: 10.1002/ptr.1111. PubMed PMID: WOS:000181973000008.
8. Bailly F, Cotelle P. Anti-HIV activities of natural antioxidant caffeic acid derivatives: Toward an antiviral supplementation diet. Current Medicinal Chemistry. 2005; 12(15):1811-8. doi: 10.2174/0929867054367239. PubMed PMID: WOS:000229763600007.
9. Mahmood N, Moore P S, Detommasi N, Desimone F, Colman S, Hay A J, et al. Inhibition of HIV-infection by Caffeoylquinic Acid-derivatives. Antiviral Chemistry & Chemotherapy. 1993; 4(4):235-40. PubMed PMID: WOS:A1993LN54900006.
10. Denzler K, Huynh T, Jacobs B, Langland J. *Melissa officinalis* extract inhibits herpes simplex virus-1 glycoprotein B interaction with heparin sulfate. Herbal Medicine: Open Access. 2016; 2:1-13. doi: 10.21767/2472-0151.100014.
11. Dubois M, Bailly F, Mbemba G, Mouscadet J F, Debyser Z, Witvrouw M, et al. Reaction of rosmarinic acid with nitrite ions in acidic conditions: Discovery of nitro- and dinitrorosmarinic acids as new anti-HIV-1 agents. Journal of Medicinal Chemistry. 2008; 51(8):2575-9. doi: 10.1021/jm7011134. PubMed PMID: WOS: 000255105600028.
12. Lin Z W, Neamati N, Zhao H, Kiryu Y, Turpin J A, Aberham C, et al. Chicoric acid analogues as HIV-1 integrase inhibitors. Journal of Medicinal Chemistry. 1999; 42(8):1401-14. doi: 10.1021/jm980531m. PubMed PMID: WOS:000079920700010.
13. Charvat T T, Lee D J, Robinson W E, Chamberlin A R. Design, synthesis, and biological evaluation of chicoric acid analogs as inhibitors of HIV-1 integrase. Bioorganic & Medicinal Chemistry. 2006; 14(13):4552-67. doi: 10.1016/j.bmc.2006.02.030. PubMed PMID: WOS: 000238182500022.
14. Mazzanti G, Battinelli L, Pompeo C, Serrilli A M, Rossi R, Sauzullo I, et al. Inhibitory activity of *Melissa officinalis* L. extract on Herpes simplex virus type 2 replication. Natural Product Research. 2008; 22(16):1433-40. doi: 10.1080/14786410802075939. PubMed PMID: WOS:000261337000008.
15. Andjelkovic M, Van Camp J, De Meulenaer B, Depaemelaere G, Socaciu C, Verloo M, et al. Iron-chelation properties of phenolic acids bearing catechol and galloyl groups. Food Chemistry. 2006; 98(1):23-31. doi: 10.1016/j.foodchem.2005.05.044. PubMed PMID: WOS: 000236539600004.
16. Rice-Evans C A, Miller N J, Paganga G. Structure-antioxidant activity relationships of flavonoids and phenolic acids. Free Radical Biology and Medicine. 1996; 20(7):933-56. doi: 10.1016/0891-5849(95)02227-9. PubMed PMID: WOS:A1996UM10600007.
17. Hider R C, Liu Z D, Khodr H H. Metal chelation of polyphenols. Flavonoids and Other Polyphenols. 2001; 335:190-203. PubMed PMID: WOS:000170554800017.

18. Moran J F, Klucas R V, Grayer R J, Abian J, Becana M. Complexes of iron with phenolic compounds from soybean nodules and other legume tissues: Prooxidant and antioxidant properties. Free Radical Biology and Medicine. 1997; 22(5):861-70. doi: 10.1016/s0891-5849(96)00426-1. PubMed PMID: WOS:A1997WD84200014.
19. Khokhar S, Apenten R K O. Iron binding characteristics of phenolic compounds: some tentative structure-activity relations. Food Chemistry. 2003; 81(1):133-40. doi: 10.1016/s0308-8146(02)00394-1. PubMed PMID: WOS:000181479600017.
20. Kontoghiorghe C N, Kolnagou A, Kontoghiorghes G J. Phytochelators Intended for Clinical Use in Iron Overload, Other Diseases of Iron Imbalance and Free Radical Pathology. Molecules. 2015; 20(11):20841-72. doi: 10.3390/molecules201119725. PubMed PMID: WOS:000365925200038.
21. Genaro-Mattos T C, Mauricio A Q, Rettori D, Alonso A, Hermes-Lima M. Antioxidant Activity of Caffeic Acid against Iron-Induced Free Radical Generation-A Chemical Approach. Plos One. 2015; 10(6). doi: 10.1371/journal.pone.0129963. PubMed PMID: WOS:000356835800047.
22. Petrou A L, Koromantzou M V, Tsangaris J M. Coordination-complexes of 3,4-dihydroxyphenylpropionic Acid (dihydrocaffeic acid) with Copper(II), Nickel(II), Cobalt (II) and Iron(III). Transition Metal Chemistry. 1991; 16(1):48-52. doi: 10.1007/bf01127870. PubMed PMID: WOS:A1991EV28900012.
23. Karaliota A, Kamariotaki M, Hadjipanagioti D, Aletras V. Molybdenum catecholates as models for Mo in biological systems. 1. Synthesis and spectroscopic study on Mo complexes with 3,4-dihydroxybenzoic and 3,4-dihydroxyphenylacetic acid. Journal of Inorganic Biochemistry. 1998; 69(1-2):79-90. doi: 10.1016/s0162-0134(97)10022-8. PubMed PMID: WOS:000074616300009.
24. Bengali Z, Townsley A C, Moss B. Vaccinia virus strain differences in cell attachment and entry. Virology. 2009; 389(1-2): 132-40. doi: 10.1016/j.virol.2009.04.012. PubMed PMID: WOS:000266948800015.
25. O'Hearn A, Wang M X, Cheng H, Lear-Rooney C M, Koning K, Rumschlag-Booms E, et al. Role of EXT1 and Glycosaminoglycans in the Early Stage of Filovirus Entry. Journal of Virology. 2015; 89(10):5441-9. doi: 10.1128/jvi.03689-14. PubMed PMID: WOS:000353329300024.
26. Shakeri A, Sahebkar A, Javadi B. *Melissa officinalis* L.—A review of its traditional uses, phytochemistry and pharmacology. Journal of Ethnopharmacology. 2016; 188:204-28. doi: 10.1016/j.jep.2016.05.010. PubMed PMID: WOS:000379560800022.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed:

1. A method of treating a subject infected with Ebola virus, the method comprising administering to the subject a complex of a compound, or a pharmaceutical composition comprising the complex in an amount to treat infection by the Ebola simplex virus in the subject, wherein the compound is and the complex comprises $Fe^{+3}$.

2. A method of treating a subject infected with herpes simplex virus, the method comprising administering to the subject a complex of a compound, or a pharmaceutical composition comprising a complex of the compound and a pharmaceutically acceptable carrier in an amount to treat infection by the herpes simplex virus in the subject, wherein the compound is:

(I)

wherein the complex comprises $Fe^{+3}$.

* * * * *

UNITED STATES PATENT AND TRADEMARK OFFICE
CERTIFICATE OF CORRECTION

| | | |
|---|---|---|
| PATENT NO. | : 11,458,203 B2 | Page 1 of 1 |
| APPLICATION NO. | : 16/612222 | |
| DATED | : October 4, 2022 | |
| INVENTOR(S) | : Thomas Cahill et al. | |

It is certified that error appears in the above-identified patent and that said Letters Patent is hereby corrected as shown below:

In the Claims

The structure in Claim 2 at Column 26, Line 40-47, should read as follows:

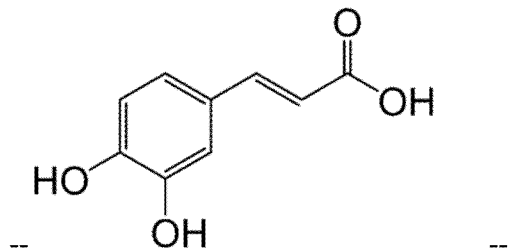

Signed and Sealed this
Fifteenth Day of August, 2023

Katherine Kelly Vidal
*Director of the United States Patent and Trademark Office*